(12) United States Patent
Montoya et al.

(10) Patent No.: US 11,773,675 B2
(45) Date of Patent: Oct. 3, 2023

(54) PRESSURIZED RESERVOIR CORE SAMPLE TRANSFER TOOL SYSTEM

(71) Applicant: Chevron U.S.A. Inc., San Ramon, CA (US)

(72) Inventors: James Daniel Montoya, Santa Fe, NM (US); Jonathon Crain Boudreaux, Santa Fe, NM (US); Patrick Rodriguez, Santa Fe, NM (US); Cole Thomas Brinkley, Santa Fe, NM (US)

(73) Assignee: CHEVRON U.S.A. INC., San Ramon, CA (US)

( * ) Notice: Subject to any disclaimer, the term of this patent is extended or adjusted under 35 U.S.C. 154(b) by 148 days.

(21) Appl. No.: 16/944,542

(22) Filed: Jul. 31, 2020

(65) Prior Publication Data

US 2021/0032947 A1    Feb. 4, 2021

Related U.S. Application Data

(60) Provisional application No. 63/050,662, filed on Jul. 10, 2020, provisional application No. 62/881,797, (Continued)

(51) Int. Cl.
*E21B 25/08* (2006.01)
*E21B 25/00* (2006.01)
(Continued)

(52) U.S. Cl.
CPC ............ *E21B 25/08* (2013.01); *E21B 25/005* (2013.01); *E21B 49/088* (2013.01); (Continued)

(58) Field of Classification Search
CPC .......... E21B 25/005; E21B 25/08; G01N 1/28
See application file for complete search history.

(56) References Cited

U.S. PATENT DOCUMENTS

| 4,317,490 A * | 3/1982 | Milberger ............... E21B 25/18 175/20 |
| 4,916,945 A * | 4/1990 | Weisbrod ................ E21B 25/08 73/863 |
| 6,305,482 B1 * | 10/2001 | Aumann ............... E21B 25/005 175/58 |
| 6,378,631 B1 * | 4/2002 | Aumann ............... E21B 25/005 175/246 |
| 8,621,920 B2 * | 1/2014 | Reid ..................... E21B 49/081 73/152.11 |

(Continued)

FOREIGN PATENT DOCUMENTS

KR    2014001408 A  *  1/2014

OTHER PUBLICATIONS

Geotek "Pressure Core Analysis" (Year: 2016).*

*Primary Examiner* — John Fitzgerald
(74) *Attorney, Agent, or Firm* — Smith & Woldesenbet Law Group, PLLC

(57) ABSTRACT

A system for transferring at least one subterranean core sample under pressure can include a retrieval vessel that collects and houses the at least one subterranean core sample at a sampling pressure at which the at least one subterranean core is collected. The system can also include a linear actuator that couples to the retrieval vessel through a valve in the open position at a first time, where the linear actuator facilitates removal of at least one pressure barrier from the retrieval vessel through the valve at the first time while maintaining the sampling pressure of the at least one subterranean sample. The system can further include a testing vessel that couples to the linear actuator through the valve in the open position at a second time, and a hydraulic device that facilitates pressurizing the testing vessel to the sampling pressure at the second time.

13 Claims, 35 Drawing Sheets

Related U.S. Application Data filed on Aug. 1, 2019, provisional application No. 62/881,787, filed on Aug. 1, 2019.

(51) Int. Cl.
| | | |
|---|---|---|
| *E21B 49/08* | (2006.01) | |
| *G01N 33/24* | (2006.01) | |
| *G01R 33/12* | (2006.01) | |
| *G01N 1/08* | (2006.01) | |
| *G01N 1/28* | (2006.01) | |

(52) U.S. Cl.
CPC ........... *E21B 49/0875* (2020.05); *G01N 1/08* (2013.01); *G01N 1/28* (2013.01); *G01N 33/24* (2013.01); *G01R 33/12* (2013.01)

(56) References Cited

U.S. PATENT DOCUMENTS

| | | | |
|---|---|---|---|
| 9,376,879 B2* | 6/2016 | Mizuguchi | E21B 25/005 |
| 9,650,891 B2* | 5/2017 | Reid | E21B 49/081 |
| 9,828,820 B2* | 11/2017 | Gupta | G01V 5/04 |
| 9,874,063 B2* | 1/2018 | Arian | E21B 27/00 |
| 10,221,684 B2* | 3/2019 | Westacott | G01V 1/306 |
| 10,246,962 B2* | 4/2019 | Gupta | E21B 49/082 |
| 10,550,655 B2* | 2/2020 | Jones | E21B 49/06 |
| 2014/0367086 A1* | 12/2014 | Arian | E21B 25/08 |
| | | | 166/69 |
| 2021/0032987 A1* | 2/2021 | Seltzer | G01R 33/12 |

\* cited by examiner

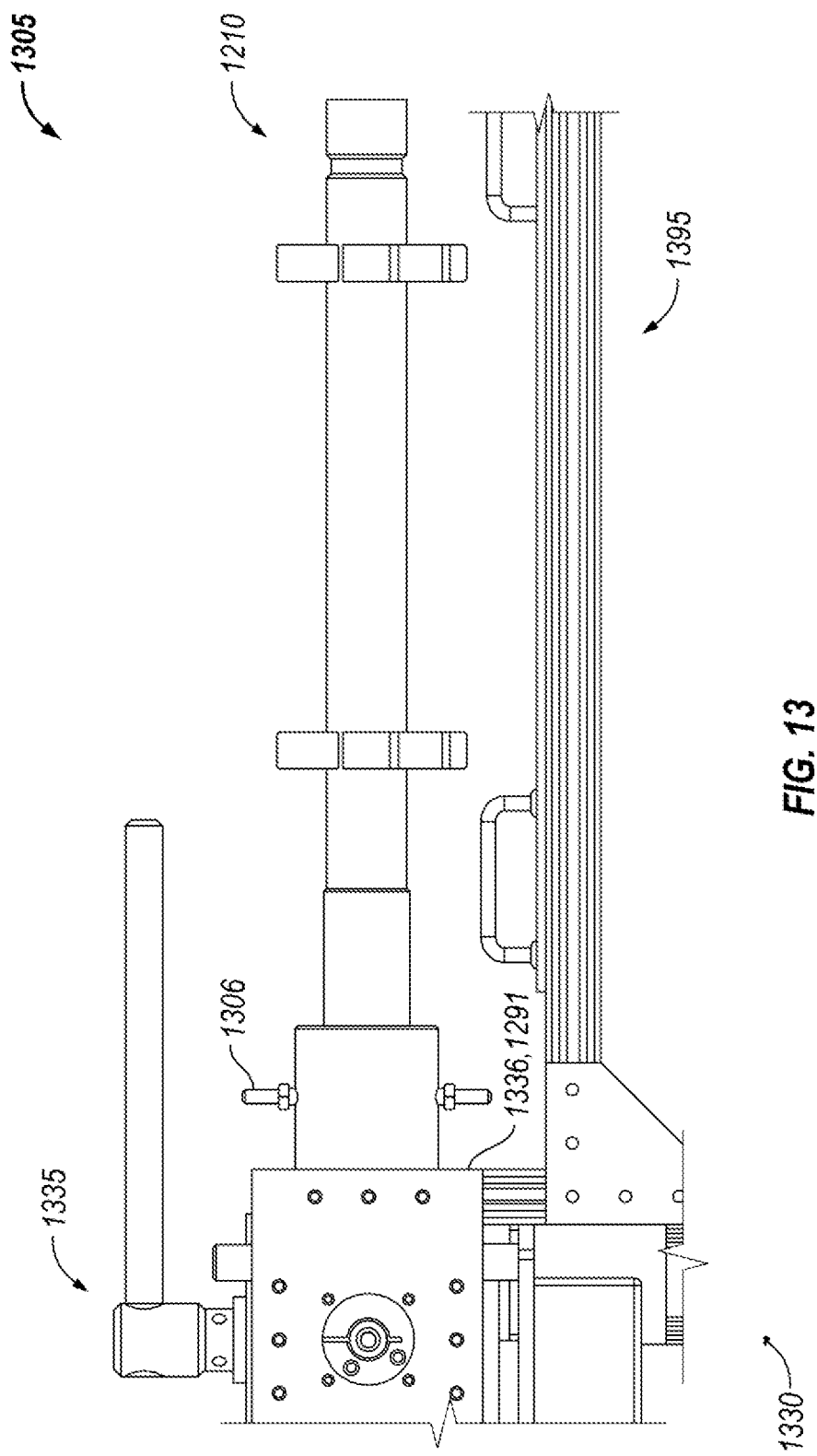

PRESSURIZED RESERVOIR CORE SAMPLE TRANSFER TOOL SYSTEM

CROSS-REFERENCE TO RELATED APPLICATIONS

This application claims priority under 35 U.S.C. § 119(e) to U.S. Provisional Patent Application No. 62/881,787, filed on Aug. 1, 2019, and titled "Pressurized Reservoir Core Sample Transfer Tool System", and to U.S. Provisional Patent Application No. 62/881,797, filed Aug. 1, 2019, and titled "Core Sample Testing," and to U.S. Provisional Patent Application No. 63/050,662, filed Jul. 10, 2020, and titled "Pressurized Reservoir Core Sample Transfer Tool System". The present application is also related to U.S. patent application Ser. No. 16/944,654, filed Jul. 31, 2020, and titled "Core Sample Testing". The entire contents of these aforementioned applications are hereby incorporated herein by reference.

TECHNICAL FIELD

The present disclosure relates generally to subterranean field operations, and more specifically to maintaining pressurized subterranean reservoir core samples for testing.

BACKGROUND

Evaluation of potential oil and gas reservoirs is highly dependent on the collection and analysis of subsurface core samples removed from wells. These cores are conventionally extracted in lengths of 30 feet or longer, each representing a continuous range of drilled depth into the formation; smaller core plugs are later cut from the core to sample at particular depths of interest. Sidewall core samples with size on the order of several inches can also be individually extracted from near the wall of the well. In either case, as the samples are returned from the well to the surface, they experience a change in pressure on the order of thousands to tens of thousands of pounds per square inch (psi), depending on the total vertical depth traveled. This pressure change affects the phase and composition of the fluids contained in the rock sample, for example causing lighter hydrocarbon molecules to volatilize and leave the sample. It may also result in structural alterations to the rock, such as the formation of fractures, changes in rock fabric, or changes in pore geometry. Laboratory core measurements are performed after these composition and structural changes have occurred, so the lab data do not necessarily represent the native state of the samples in their original downhole environment.

Within the last several years, coring systems have been introduced that can enclose up to 10-12 sidewall cores during the trip to the surface, capturing all fluids expelled from the cores due to the pressure decrease, so that they may be characterized, and the original fluid composition better understood. More recently, coring systems that maintain pressure inside the vessel while surfacing have been introduced, so as to minimize the changes to fluid composition in the samples; temperature is not maintained, so the pressure does decrease, but it remains significantly higher than atmospheric pressure. In addition, there are commercially available tools that retrieve conventional core samples while maintaining in-situ pressure, that provides samples up to 3 meters in length. However, here we focus on sidewall cores because they do not need to be subsampled for laboratory analysis, which is challenging and hazardous at elevated pressure.

Data based on directly measured reservoir properties, such as fluid content and producibility, taken from reservoir core samples in a laboratory can be utilized to inform production decisions. However, conventional tools must currently be depressurized to atmospheric pressure before the samples can be removed for laboratory study, although the gases expelled during depressurization can be collected for analysis during the process. Therefore, these core samples may not be fully representative of downhole conditions by the time they reach the laboratory, due to potential changes in pressure, fluid composition, and/or physical damage. In addition, these commercially available pressurized coring tools are known to be incompatible with certain laboratory measurements. For example, nuclear magnetic resonance (NMR) measurements require the application of radio-frequency magnetic pulses that are shielded by metal, but the existing tools are constructed from metal.

Accordingly, there is a need for a system for transferring samples from a commercial pressurized coring tool to a pressurized core holder that would be compatible with NMR, CT, and potentially other laboratory measurements, while maintaining the initial received pressure.

SUMMARY

In general, in one aspect, the disclosure relates to a system for transferring at least one subterranean core sample under pressure. The system can include a retrieval vessel that collects and houses the at least one subterranean core sample at a sampling pressure at which the at least one subterranean core sample is collected. The system can also include a valve having an open position and a closed position. The system can further include a linear actuator that couples to the retrieval vessel through the valve when the valve is in the open position at a first time, where the linear actuator facilitates removal of at least one pressure barrier from the retrieval vessel through the valve at the first time while maintaining the sampling pressure of the at least one subterranean sample. The system can also include a testing vessel that couples to the linear actuator through the valve when the valve is in the open position at a second time. The system can further include a hydraulic device that facilitates pressurizing the testing vessel to the sampling pressure at the second time. The testing vessel and the retrieval vessel can be coupled to each other through the valve at a third time, where the at least one subterranean core sample is transferred from the retrieval vessel through the valve to the testing vessel at the third time at the sampling pressure when the valve is in the open position. The linear actuator can install a pressure barrier in the testing vessel. The at least one subterranean core sample, once transferred to the testing vessel, is tested at a fourth time while in the testing vessel at the sampling pressure.

In another aspect, the disclosure can generally relate to a method of transferring at least one subterranean core sample from a retrieval vessel to a testing vessel. The method can include removing at least one pressure barrier on the retrieval vessel using a linear actuator while maintaining a sampling pressure on the at least one subterranean core sample at which the at least one subterranean core sample is taken from a subterranean formation. The method can also include pressurizing the testing vessel to the sampling pressure using the linear actuator. The method can further include transferring the at least one subterranean core sample from the retrieval vessel to the testing vessel. The method can also include sealing the testing vessel with the at least one subterranean core sample at the sampling pressure, where the testing vessel allows the at least one subterranean core sample to be tested while the at least one subterranean core sample is maintained at the sampling pressure.

In yet another aspect, a method of transferring a core sample from a retrieval vessel to a testing vessel includes transferring at least a portion of the core sample from the retrieval vessel to the testing vessel, wherein the core sample is maintained at a substantially equivalent pressure or placed under a higher pressure during the transfer of the core sample from the retrieval vessel to the testing vessel.

These and other aspects, objects, features, and embodiments will be apparent from the following description and the appended claims.

BRIEF DESCRIPTION OF THE DRAWINGS

The drawings illustrate only example embodiments of methods, systems, and devices for tool systems for transferring pressurized reservoir core samples and are therefore not to be considered limiting of its scope, as tool systems for transferring pressurized reservoir core samples may admit to other equally effective embodiments. The elements and features shown in the drawings are not necessarily to scale, emphasis instead being placed upon clearly illustrating the principles of the example embodiments. Additionally, certain dimensions or positions may be exaggerated to help visually convey such principles. In the drawings, reference numerals designate like or corresponding, but not necessarily identical, elements.

FIGS. 12A through 21 show a method for transferring pressurized reservoir core samples in accordance with certain example embodiments.

DETAILED DESCRIPTION OF EXAMPLE EMBODIMENTS

Figure 1:
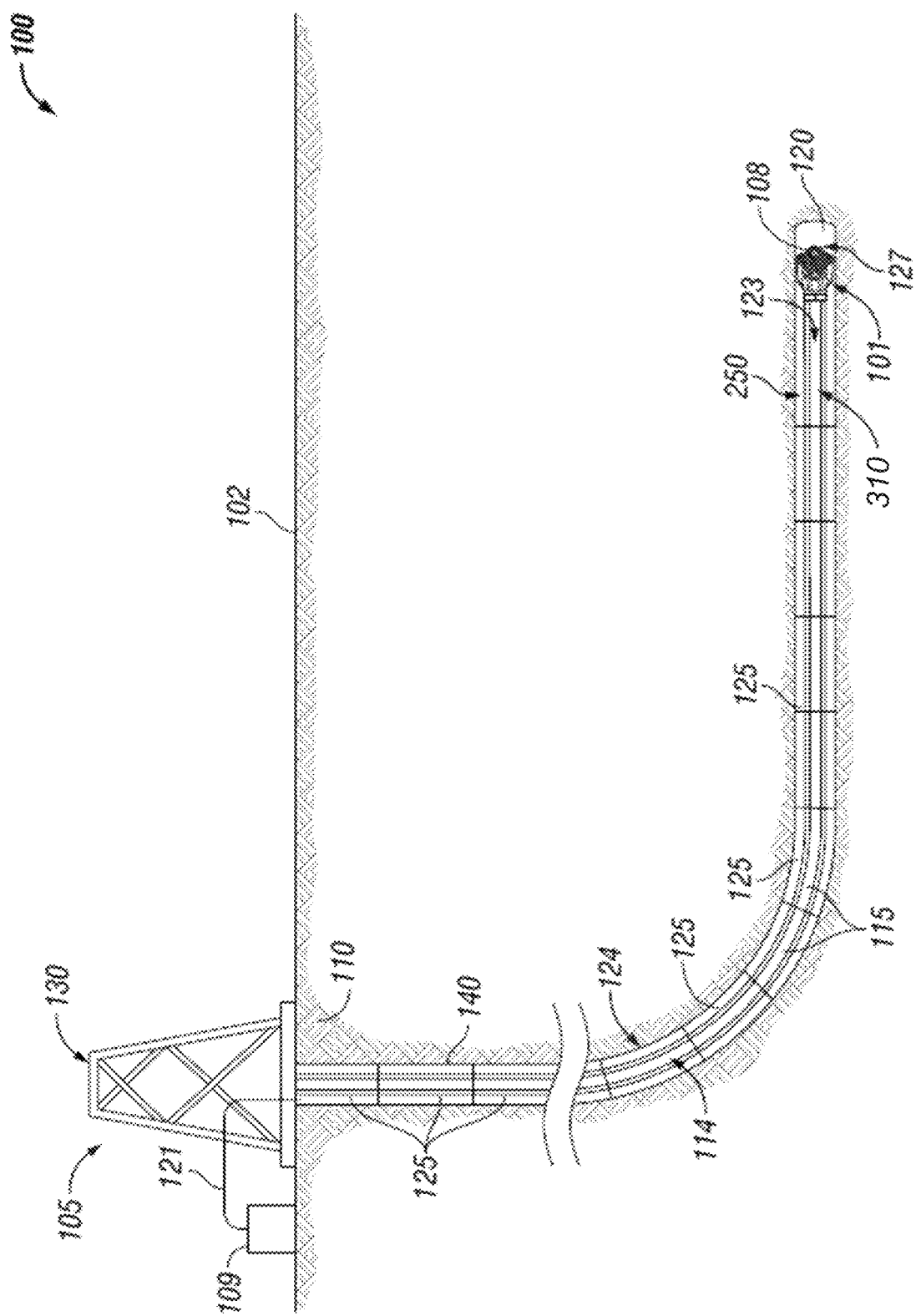
FIG. 1 shows a schematic diagram of a field system in which pressurized reservoir core samples are collected and which are later transferred under pressure in accordance with certain example embodiments.

The example embodiments discussed herein are directed to systems, apparatuses, and methods of tool systems for transferring pressurized reservoir core samples. While the example tool systems shown in the figures and described herein are directed to use with samples taken from a subterranean wellbore, example tool systems can also be used in other applications, aside from a wellbore, in which pressurized core samples are taken. Thus, the examples of tool systems for transferring pressurized reservoir core samples described herein are not limited to pressurized core samples taken in a subterranean wellbore or within a reservoir within a subterranean formation.

A user as described herein may be any person that is involved with a field operation in a subterranean wellbore and/or a retrieving or analyzing pressurized sidewall core samples within the subterranean wellbore for a field system. Examples of a user may include, but are not limited to, a roughneck, a company representative, a drilling engineer, a tool pusher, a service hand, a field engineer, an electrician, a mechanic, an operator, a consultant, a contractor, and a manufacturer's representative. In an automated system, a user can be a controller (e.g., controller 204).

Any example tool system for transferring pressurized reservoir core samples, or portions (e.g., components) thereof, described herein can be made from a single piece (as from a mold). When an example tool system for transferring pressurized reservoir core samples, or portions thereof, is made from a single piece, the single piece can be cut out, bent, stamped, and/or otherwise shaped to create certain features, elements, or other portions of a component. Alternatively, an example tool system for transferring pressurized reservoir core samples (or portions thereof) can be made from multiple pieces that are mechanically coupled to each other. In such a case, the multiple pieces can be mechanically coupled to each other using one or more of a number of coupling methods, including but not limited to adhesives, welding, fastening devices, compression fittings, mating threads, and slotted fittings. One or more pieces that are mechanically coupled to each other can be coupled to each other in one or more of a number of ways, including but not limited to fixedly, hingedly, removeably, slidably, and threadably.

Components and/or features described herein can include elements that are described as coupling, fastening, securing, or other similar terms. Such terms are merely meant to distinguish various elements and/or features within a component or device and are not meant to limit the capability or function of that particular element and/or feature. For example, a feature described as a "coupling feature" can couple, secure, fasten, and/or perform other functions aside from merely coupling. In addition, each component and/or feature described herein (including each component of an example subterranean coring assembly) can be made of one or more of a number of suitable materials, including but not limited to metal (e.g., stainless steel), ceramic, rubber, plastic, resin, fiberglass, and thermoplastic.

A coupling feature (including a complementary coupling feature) as described herein can allow one or more components and/or portions of an example tool system for transferring pressurized reservoir core samples (e.g., a flow regulating device) to become mechanically coupled, directly or indirectly, to another portion (e.g., a wall) of the tool system for transferring pressurized reservoir core samples. A coupling feature can include, but is not limited to, a portion of a hinge, an aperture, a recessed area, a protrusion, a slot, a spring clip, a tab, a detent, and mating threads. One portion of an example tool system for transferring pressurized reservoir core samples can be coupled to another portion of the tool system for transferring pressurized reservoir core samples by the direct use of one or more coupling features.

In addition, or in the alternative, a portion of an example tool system for transferring pressurized reservoir core samples can be coupled to another portion of the tool system for transferring pressurized reservoir core samples using one or more independent devices that interact with one or more coupling features disposed on a component of the tool system for transferring pressurized reservoir core samples. Examples of such devices can include, but are not limited to, a pin, a hinge, a gimbal, a fastening device (e.g., a bolt, a screw, a rivet), and a spring. One coupling feature described herein can be the same as, or different than, one or more other coupling features described herein. A complementary coupling feature as described herein can be a coupling feature that mechanically couples, directly or indirectly, with another coupling feature.

In certain example embodiments, retrieval vessels and example tool systems for transferring pressurized reservoir core samples are subject to meeting certain standards and/or requirements. For example, the American Petroleum Institute (API), the American Society of Mechanical Engineers (ASME), the International Standards Organization (ISO), and the Occupational Health and Safety Administration (OSHA) set standards for subterranean field operations and for testing vessels under high pressure (e.g., 5,000 psi). Use of example embodiments described herein meet (and/or allow a corresponding device to meet) such standards when required.

If a component of a figure is described but not expressly shown or labeled in that figure, the label used for a corresponding component in another figure can be inferred to that component. Conversely, if a component in a figure is labeled but not described, the description for such component can be substantially the same as the description for the corresponding component in another figure. The numbering scheme for the various components in the figures herein is such that each component is a three digit number and corresponding components in other figures have the identical last two digits. For any figure shown and described herein, one or more of the components may be omitted, added, repeated, and/or substituted. Accordingly, embodiments shown in a particular figure should not be considered limited to the specific arrangements of components shown in such figure.

Further, a statement that a particular embodiment (e.g., as shown in a figure herein) does not have a particular feature or component does not mean, unless expressly stated, that such embodiment is not capable of having such feature or component. For example, for purposes of present or future claims herein, a feature or component that is described as not being included in an example embodiment shown in one or more particular drawings is capable of being included in one or more claims that correspond to such one or more particular drawings herein.

Example embodiments of tool systems for transferring pressurized reservoir core samples will be described more fully hereinafter with reference to the accompanying drawings, in which example embodiments of tool systems for transferring pressurized reservoir core samples are shown. Tool systems for transferring pressurized reservoir core samples may, however, be embodied in many different forms and should not be construed as limited to the example embodiments set forth herein. Rather, these example embodiments are provided so that this disclosure will be thorough and complete, and will fully convey the scope of tool systems for transferring pressurized reservoir core samples to those of ordinary skill in the art. Like, but not necessarily the same, elements in the various figures are denoted by like reference numerals for consistency.

Terms such as "first", "second", "end", "inner", "outer", "top", "bottom", "upward", "downward", "up", "down", "distal", and "proximal" are used merely to distinguish one component (or part of a component or state of a component) from another. Such terms are not meant to denote a preference or a particular orientation. Also, the names given to various components described herein are descriptive of one embodiment and are not meant to be limiting in any way. Those of ordinary skill in the art will appreciate that a feature and/or component shown and/or described in one embodiment (e.g., in a figure) herein can be used in another embodiment (e.g., in any other figure) herein, even if not expressly shown and/or described in such other embodiment.

FIG. 1 shows a schematic diagram of a land-based field system 100 in which pressurized reservoir core samples can be taken within a subterranean wellbore in accordance with one or more example embodiments. Referring to FIG. 1, the field system 100 in this example includes a wellbore 120 that is formed by a wall 140 in a subterranean formation 110 using field equipment 130. The field equipment 130 can be located above a surface 102, and/or within the wellbore 120. The surface 102 can be ground level for an on-shore application and the sea floor for an off-shore application. The point where the wellbore 120 begins at the surface 102 can be called the entry point.

The subterranean formation 110 can include one or more of a number of formation types, including but not limited to shale, limestone, sandstone, clay, sand, and salt. In certain embodiments, a subterranean formation 110 can also include one or more reservoirs in which one or more resources (e.g., oil, gas, water, steam) can be located. One or more of a number of field operations (e.g., coring, tripping, drilling, setting casing, extracting downhole resources) can be performed to reach an objective of a user with respect to the subterranean formation 110.

The wellbore 120 can have one or more of a number of segments, where each segment can have one or more of a number of dimensions. Examples of such dimensions can include, but are not limited to, size (e.g., diameter) of the wellbore 120, a curvature of the wellbore 120, a total vertical depth of the wellbore 120, a measured depth of the wellbore 120, and a horizontal displacement of the wellbore 120. The field equipment 130 can be used to create and/or develop (e.g., insert casing pipe, extract downhole materials) the wellbore 120. The field equipment 130 can be positioned and/or assembled at the surface 102. The field equipment 130 can include a derrick, a tool pusher, a clamp, a tong, drill pipe, a drill bit, the retrieval vessel 310, tubing pipe 115, a power source, and casing pipe 125.

The field equipment 130 can also include one or more devices that measure and/or control various aspects (e.g., direction of wellbore 120, pressure, temperature) of a field operation associated with the wellbore 120. For example, the field equipment 130 can include a wireline tool that is run through the wellbore 120 to provide detailed information (e.g., curvature, azimuth, inclination) throughout the wellbore 120. Such information can be used for one or more of a number of purposes. For example, such information can dictate the size (e.g., outer diameter) of casing pipe to be inserted at a certain depth in the wellbore 120.

Inserted into and disposed within the wellbore 120 of FIG. 1 are a number of casing pipes 125 that are coupled to each other to form the casing string 124. In this case, each end of a casing pipe 125 has mating threads (a type of coupling feature) disposed thereon, allowing a casing pipe 125 to be mechanically coupled to an adjacent casing pipe 125 in an end-to-end configuration. The casing pipes 125 of the casing string 124 can be mechanically coupled to each other directly or using a coupling device, such as a coupling sleeve. The casing string 124 is not disposed in the entire wellbore 120. Often, the casing string 124 is disposed from approximately the surface 102 to some other point in the wellbore 120. The open hole portion 127 of the wellbore 120 extends beyond the casing string 124 at the distal end of the wellbore 120.

Each casing pipe 125 of the casing string 124 can have a length and a width (e.g., outer diameter). The length of a casing pipe 125 can vary. For example, a common length of a casing pipe 125 is approximately 40 feet. The length of a casing pipe 125 can be longer (e.g., 60 feet) or shorter (e.g., 10 feet) than 40 feet. The width of a casing pipe 125 can also vary and can depend on the cross-sectional shape of the casing pipe 125. For example, when the cross-sectional shape of the casing pipe 125 is circular, the width can refer to an outer diameter, an inner diameter, or some other form of measurement of the casing pipe 125. Examples of a width in terms of an outer diameter can include, but are not limited to, 7 inches, 7⅝ inches, 8⅝ inches, 10¾ inches, 13⅜ inches, and 14 inches.

The size (e.g., width, length) of the casing string 124 can be based on the information gathered using field equipment 130 with respect to the wellbore 120. The walls of the casing string 124 have an inner surface that forms a cavity 123 that traverses the length of the casing string 124. Each casing pipe 125 can be made of one or more of a number of suitable materials, including but not limited to stainless steel. In certain example embodiments, each casing pipe 125 is made of one or more of a number of electrically conductive materials.

A number of tubing pipes 115 that are coupled to each other and inserted inside the cavity 123 form the tubing string 114. The collection of tubing pipes 115 can be called a tubing string 114. The tubing pipes 115 of the tubing string 114 are mechanically coupled to each other end-to-end, usually with mating threads (a type of coupling feature). The tubing pipes 115 of the tubing string 114 can be mechanically coupled to each other directly or using a coupling device. Each tubing pipe 115 of the tubing string 114 can have a length and a width (e.g., outer diameter). The length of a tubing pipe 115 can vary. For example, a common length of a tubing pipe 115 is approximately 30 feet. The length of a tubing pipe 115 can be longer (e.g., 40 feet) or shorter (e.g., 10 feet) than 30 feet. Also, the length of a tubing pipe 115 can be the same as, or different than, the length of an adjacent casing pipe 125.

The width of a tubing pipe 115 can also vary and can depend on one or more of a number of factors, including but not limited to the target depth of the wellbore 120, the total length of the wellbore 120, the inner diameter of the adjacent casing pipe 125, and the curvature of the wellbore 120. The width of a tubing pipe 115 can refer to an outer diameter, an inner diameter, or some other form of measurement of the tubing pipe 115. Examples of a width in terms of an outer diameter for a tubing pipe 115 can include, but are not limited to, 7 inches, 5 inches, and 4 inches.

In some cases, the outer diameter of the tubing pipe 115 can be such that a gap exists between the tubing pipe 115 and an adjacent casing pipe 125. The walls of the tubing pipe 115 have an inner surface that forms a cavity that traverses the length of the tubing pipe 115. The tubing pipe 115 can be made of one or more of a number of suitable materials, including but not limited to steel.

At the distal end of the tubing string 114 within the wellbore 120 is a bottomhole assembly (BHA) 101. The BHA 101 can include a retrieval vessel 310. Alternatively, the retrieval vessel 310 can be further uphole and integrated with the tubing pipes 115 as part of the tubing string 114. The retrieval vessel 310 is used to obtain and retain a sample (a core) of the subterranean formation 110, either in the open hole portion 127 of the wellbore 120 or through the casing string 124, by cutting into the formation 110. The BHA 101 can also include one or more other components, including but not limited to one or more tubing pipes 115 and one or more stabilizers.

Figure 2:
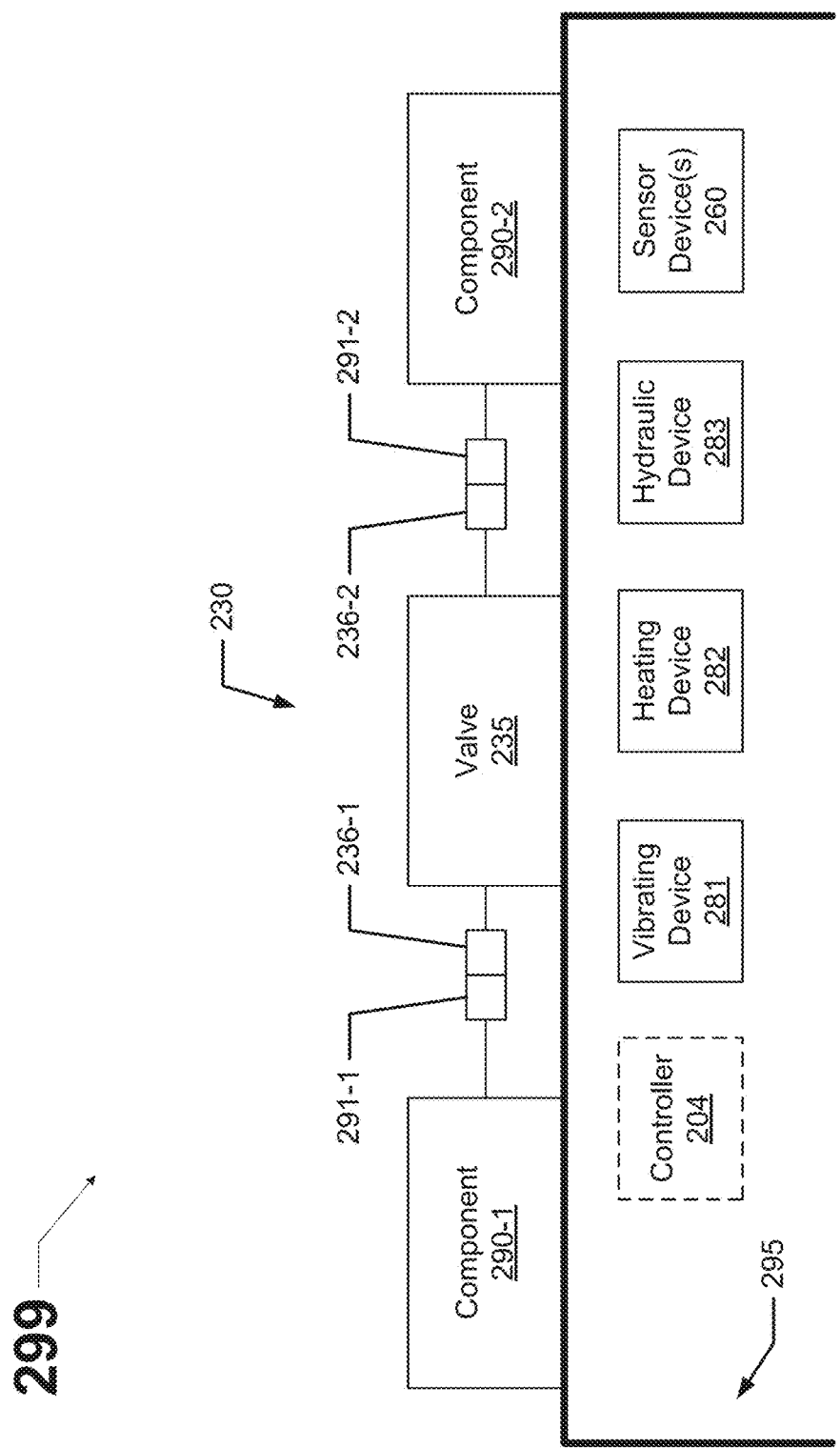
FIG. 2 shows a general tool system for transferring pressurized reservoir core samples in accordance with certain example embodiments.

FIG. 2 shows a general tool system 299 for transferring pressurized reservoir core samples in accordance with certain example embodiments. Referring to FIGS. 1 and 2, the system 299 of FIG. 2 includes a frame 295 upon which a valve assembly 230 (which includes a valve 235), a component 290-1, and another component 290-2 are mounted. As shown below, the valve assembly 230 can be mounted on a gimbal to enable a rotational degree of freedom that moves the valve assembly 230 and the components 290 coupled thereto to move between a vertical orientation and a horizontal orientation, where the vertical orientation helps facilitate the transfer of the subterranean core samples by way of gravitational loading. The valve 235 of the valve assembly 230 is coupled to and disposed between component 290-1 and component 290-2. Specifically, the valve 235 has two coupling features 236. Coupling feature 236-1 couples (directly or indirectly) to a coupling feature 291-1 of component 290-1, and coupling feature 236-2 couples (directly or indirectly) to a coupling feature 291-2 of component 290-2. These coupling features 236 and coupling features 291 can be, for example, one or more threaded apertures (into which one or more bolts can be inserted) or mating threads.

Component 290-1 and component 290-2 are interchangeable parts of the system 299. As such, the corresponding coupling features 291 are detachably coupled to the coupling features 236 of the valve 235. In the example systems described herein, a component 290 can be a retrieval vessel 310 (first appearing in FIGS. 3A through 3D), a linear actuator 320 (first appearing in FIGS. 3A through 3D), and a testing vessel 740 (first appearing in FIGS. 7A through 7D). Each of these components 290 can include any of a number of modifications (e.g., addition of an adapter) to allow the component 290 to become detachably coupled to the valve 235. The various components 290 are moved and/or replaced during different steps in the process of transferring pressurized subterranean core samples from the retrieval vessel 310 to the testing vessel 740.

Before, during, and after the transfer of the core samples from the retrieval vessel 320 to the testing vessel 740, the core samples are maintained at a substantially equivalent pressure or placed under a higher pressure relative to the pressure of the subterranean formation from which the core samples are taken. By doing so, the subsequent testing, conducted on the core samples while they are disposed within the testing vessel 740 under pressure, and the corresponding test results may be more accurate (e.g., more representative of reservoir conditions). For example, embodiments consistent with the present disclosure may be utilized for characterizing the core samples and their fluid contents, both while at the initial received pressure and during the depressurization process.

Furthermore, embodiments consistent with the present disclosure may be utilized for characterizing core samples that have been recovered and maintained at elevated pressure and/or temperature. In certain embodiments, the core samples can be maintained at the original reservoir pressure and/or temperature through retrieval, transfer, and testing, so that there are minimal or no structural changes to the samples, and/or minimal or no changes to the composition and phase of the fluids contained in the samples. In certain other example embodiments, representative conditions may refer to when the core samples have been maintained at an elevated pressure and/or temperature that is/are representative of the original reservoir pressure and/or temperature, such that the fluids contained in the core samples have not undergone a phase transition (e.g., at a bubble point or dew point) and the fluid contents of the samples remain representative of reservoir conditions. Additionally, in certain embodiments, representative conditions may refer to the structure of the core samples having changed less than if the pressure and/or temperature had been allowed to reach ambient conditions.

The valve 235 can be any type of valve, including but not limited to a ball valve, a plug valve, a pinch valve, and a gate valve. The valve 235 can be linear (as in this case) so that component 290-1 and component 290-2 are axially aligned and accessible to each other through the valve 235 when the valve 235 is an a fully open position. The valve 235 can be operated manually (e.g., using a handle) or automatically (e.g., using the optional controller 204). The valve 235 can have a fully open position, a closed position, and any of a number of partially open positions. The valve 235 can be substantial enough in structure to withstand the high pressures (e.g., 5000 psi, 10000 psi) at which the pressurized subterranean core samples are typically maintained.

The system 299 can also include one or more of a number of other devices. For example, the system 299 can include one or more sensor devices 260, a vibrating device 281, a heating device 282, a hydraulic device 283, and an optional controller 204. A sensor device can include any type of sensor that measures one or more parameters. Examples of types of sensor devices 260 can include, but are not limited to, a fluid flow meter, a pressure sensor, an air flow monitor, a torque sensor, a gas detector, and a resistance temperature detector. Examples of a parameter that is measured by a sensor device 260 can include, but are not limited to, a temperature, a level of gas, a level of humidity, a flow rate, and a pressure wave. Measurements taken by a sensor device 260 can be delivered to the optional controller 204 for processing.

A heating device 282 can provide a controlled amount of heat to one or more parts of the system 299. For example, when component 290-2 is retrieval vessel 310 filled with pressurized reservoir core samples (also called pressurized subterranean core samples herein), the heating device 282 can apply heat to the retrieval vessel 310 to make at least some of the fluid contents of the retrieval vessel 320 less viscous and help initiate and propagate movement of the core samples out of the retrieval vessel 310 to the testing vessel 740. The heating device 282 can be controlled manually or by the optional controller 204.

The vibrating device 281 is configured to apply vibrations to one or more parts of the system 299. For example, when component 290-1 is retrieval vessel 310 filled with pressurized reservoir core samples (also called pressurized subterranean core samples, subterranean core samples, or core samples herein) and reservoir fluids, the vibrating device 281 can apply vibrational mechanical energy to the retrieval vessel 310 to help initiate and propagate movement of the core samples out of the retrieval vessel 310 to the testing vessel 740. The vibrating device 281 can be controlled manually or by the optional controller 204 to any required frequency of vibration.

The hydraulic device 283 is designed to control the pressure within one or more parts of the system 299. The hydraulic device 283 can include one or more pieces of equipment, including but not limited to a motor, a compressor, a pump, piping, fittings, and tubing. The hydraulic device 283 can be used to equalize and maintain a sampling pressure of the core samples within the retrieval vessel 310 or the testing vessel 740. The hydraulic device 283 can also be used to fill and pressurize fluid within a part (e.g., the testing vessel 740 before receiving the core samples) of the system 299.

The optional controller 204 can be used to control some or all of the system 299. For example, the controller 204 can control the heating device 282, a motor (e.g., for the vibrating device 281, for the hydraulic device 283), and/or another other component of the system 299. The controller 204 can include one or more of a number of components. Such components can include, but are not limited to, an electrical motor (e.g., stepper, servo), torque sensor feedback, a control engine, a communication module, a timer, an energy metering module, a power module, a hardware processor, memory, a transceiver, an application interface, an energy storage device, one or more switches, a storage repository, and a security module. The controller 204 can correspond to a computer system as described below with regard to FIG. 23. The components shown in FIG. 2 are not exhaustive, and in some embodiments, one or more of the components shown in FIG. 2 may not be included in an example system 299. Any component of the example system 299 can be discrete or combined with one or more other components of the system 299.

The frame 295 can be any type of suitable structure having any of a number of features and/or components to facilitate all steps in the process of transferring pressurized subterranean core samples from the retrieval vessel 310 to the testing vessel 740. For example, in addition to allowing for the replacement of components 290, the frame 295 can allow for the movement (e.g., rotation) of one or more components 290 and/or the valve assembly 230 (including portions thereof). For example, the frame 295 can include a gimbal (e.g., gimbal 331 shown in FIGS. 3A through 3D below) to which the valve assembly 230 is coupled, allowing the valve assembly 230 to rotate.

Figure 3A:
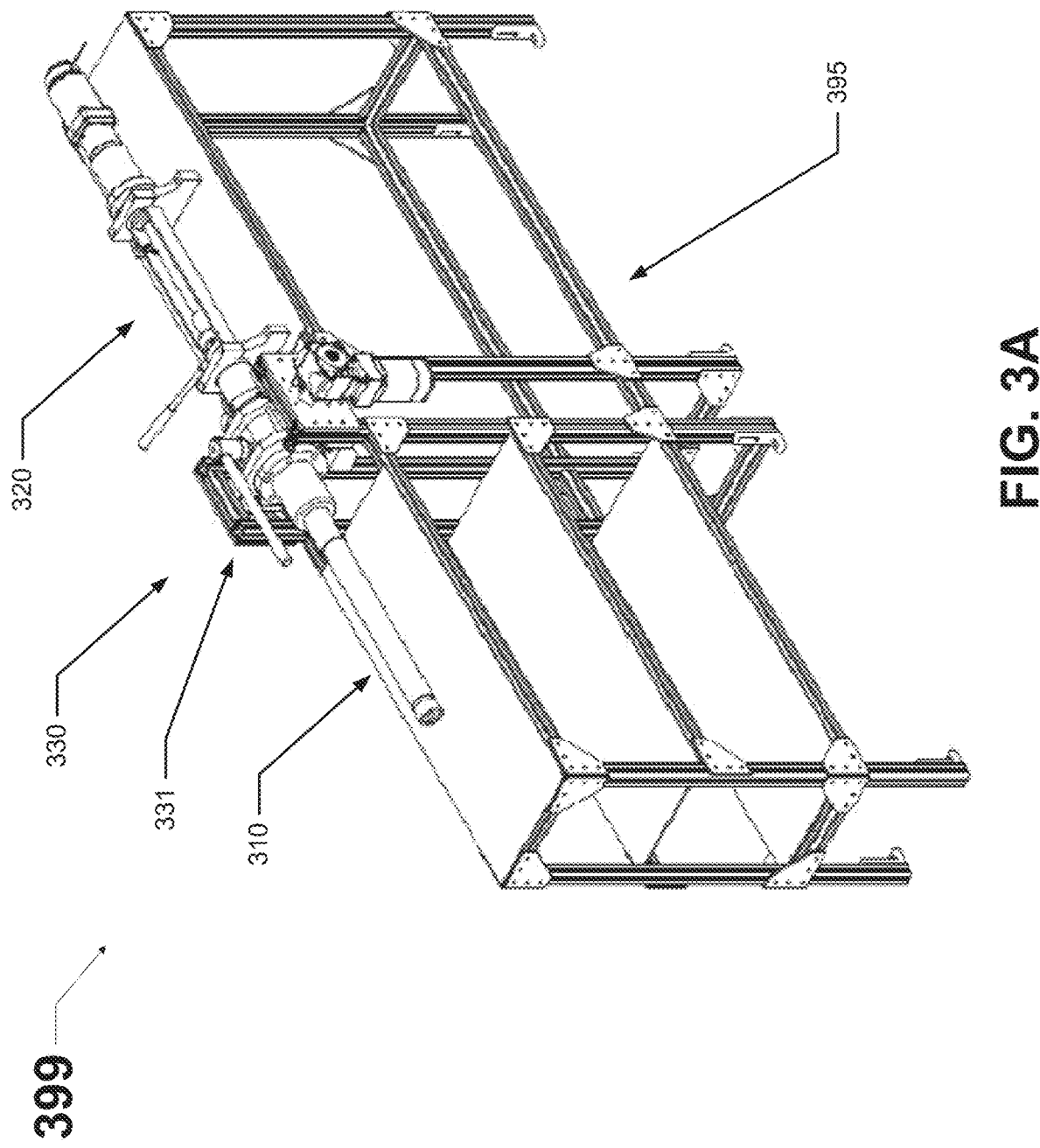
FIGS. 3A through 3D show various views of a tool system for transferring pressurized reservoir core samples at a point in time in accordance with certain example embodiments.
Figure 3B:
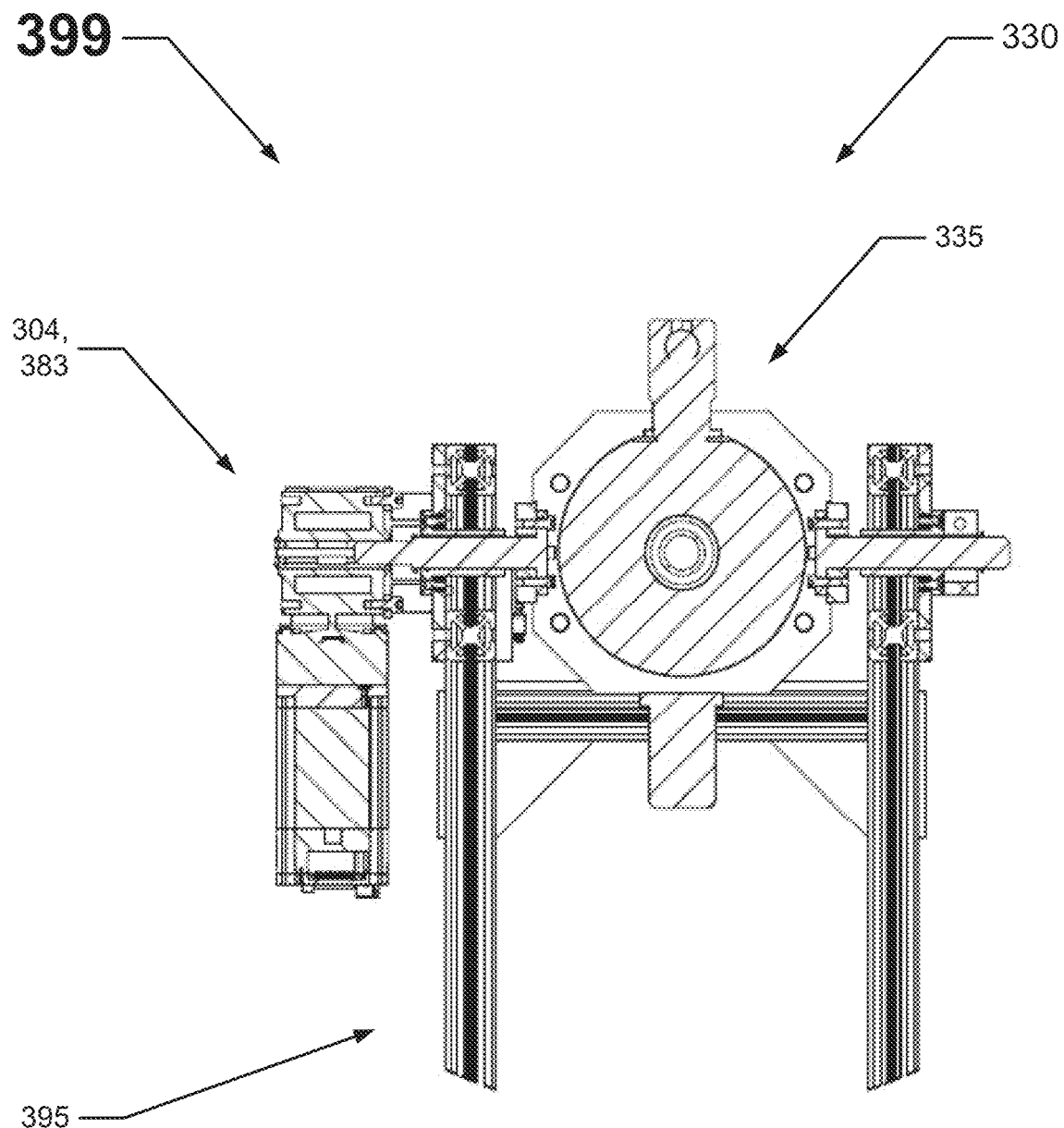
Figure 3C:
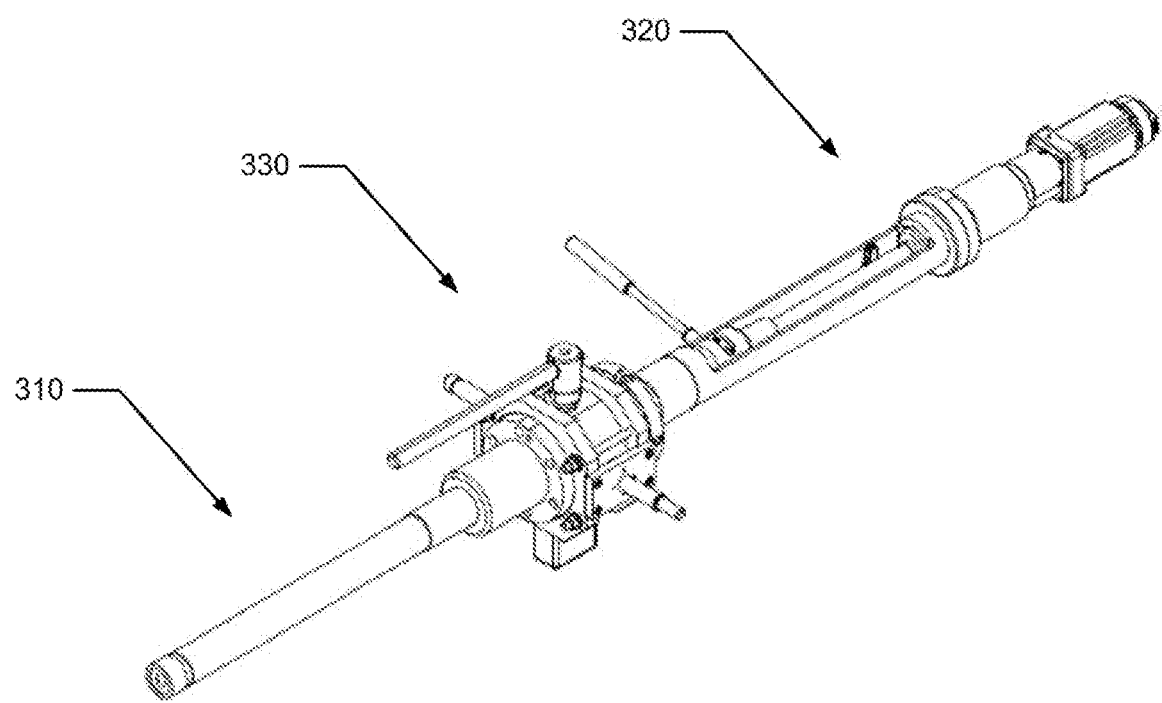
Figure 3D:
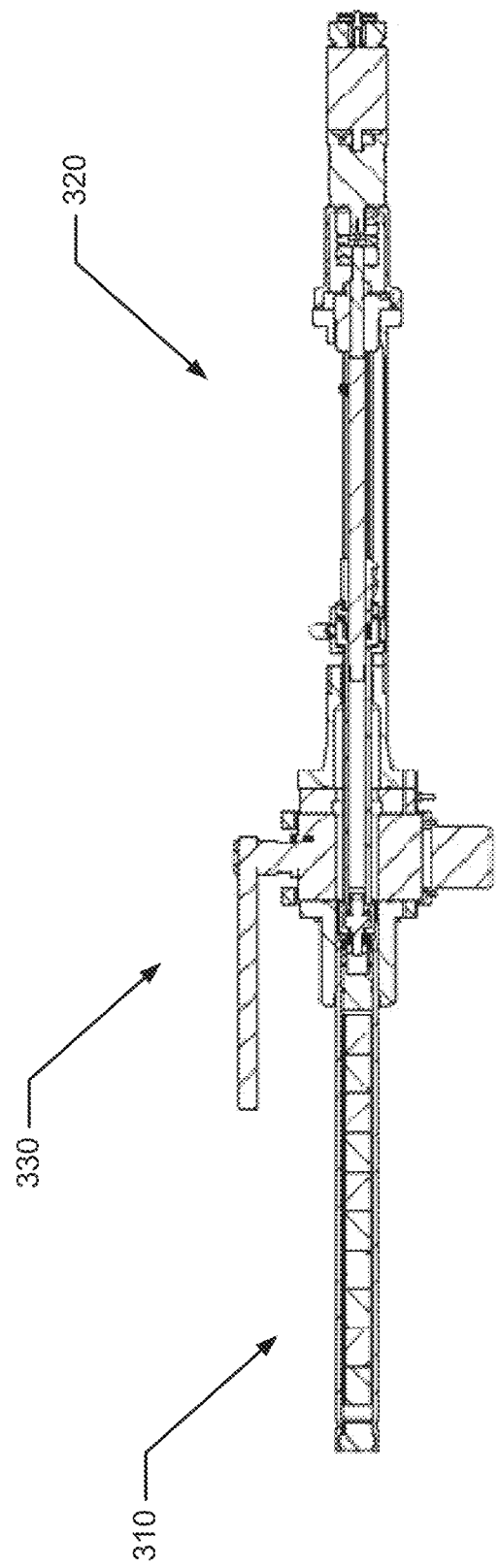

FIGS. 3A through 3D show various views of a tool system 399 for transferring pressurized reservoir core samples at a point in time in accordance with certain example embodiments. Specifically, FIG. 3A shows an isometric perspective view of the system 399. FIG. 3B shows a cross-sectional front view of the system 399. FIG. 3C shows an isometric perspective view of an assembly of the retrieval vessel 310, the valve assembly 330 (which includes a valve 335), and the linear actuator 320. FIG. 3D shows a cross sectional side view of the assembly of FIG. 3C. Referring to FIGS. 1 through 3D, the parts (e.g., the frame 395, the valve assembly 330) of the system 399 of FIGS. 3A through 3D are substantially the same as the corresponding parts of the system 299 of FIG. 2 above. Also, the configuration of the system 399 of FIGS. 3A through 3D is a configuration of the system 299 shown in FIG. 2.

The system 399 also includes a controller 304 and a hydraulic device 383, as shown in FIG. 3B. A gear-actuated gimbal system 331 can be utilized to enable a rotational degree of freedom which can rotate the valve assembly 330 from a horizontal to a vertical orientation to help facilitate transfer of core samples by way of gravitational loading. The gimbal system 331 can be manually or electrically actuated (e.g., by a gearmotor) and controlled (e.g., by the controller 304). Since the retrieval vessel 310 and the linear actuator 320 are detachably coupled to the valve 335 of the valve assembly 330, the retrieval vessel 310 and the linear actuator 320 are considered components (e.g., components 290). The retrieval vessel 310 is designed to collect and/or house one or more pressurized subterranean core samples and reservoir fluids taken from the sidewall of a wellbore. The retrieval vessel 310 is removed from a BHA or general core retrieval tooling for use in the example system 399. The retrieval vessel 310 is known in the art. The retrieval vessel 310 is made of magnetic and/or metallic material. As a result, it is not possible to test the pressurized subterranean core samples disposed within the retrieval vessel 310 using technologies such as NMR. Example embodiments are designed to transfer the subterranean core samples under the same pressure to a testable vessel, which is non-metallic and/or non-magnetic.

The linear actuator 320 is configured to perform one or more functions associated with removing pressure barriers (e.g., a plug, a spring, a piston head) from the retrieval vessel 310 while maintaining the high sampling pressure within the retrieval vessel 310. In this case, the linear actuator 320 works through the valve 335 when the valve 335 is in a fully open (or near fully open) position. In certain example embodiments, the linear actuator 320 is designed to integrate one or more tools (e.g., a spring extractor, piston removal device) that are used to prepare or otherwise internally access the retrieval vessel 310 and/or the testing vessel 740 for the transfer of pressurized subterranean core samples while maintaining initial pressure of the retrieval vessel 310. Details of an example linear actuator 320 are provided below with respect to FIG. 4.

Figure 4:
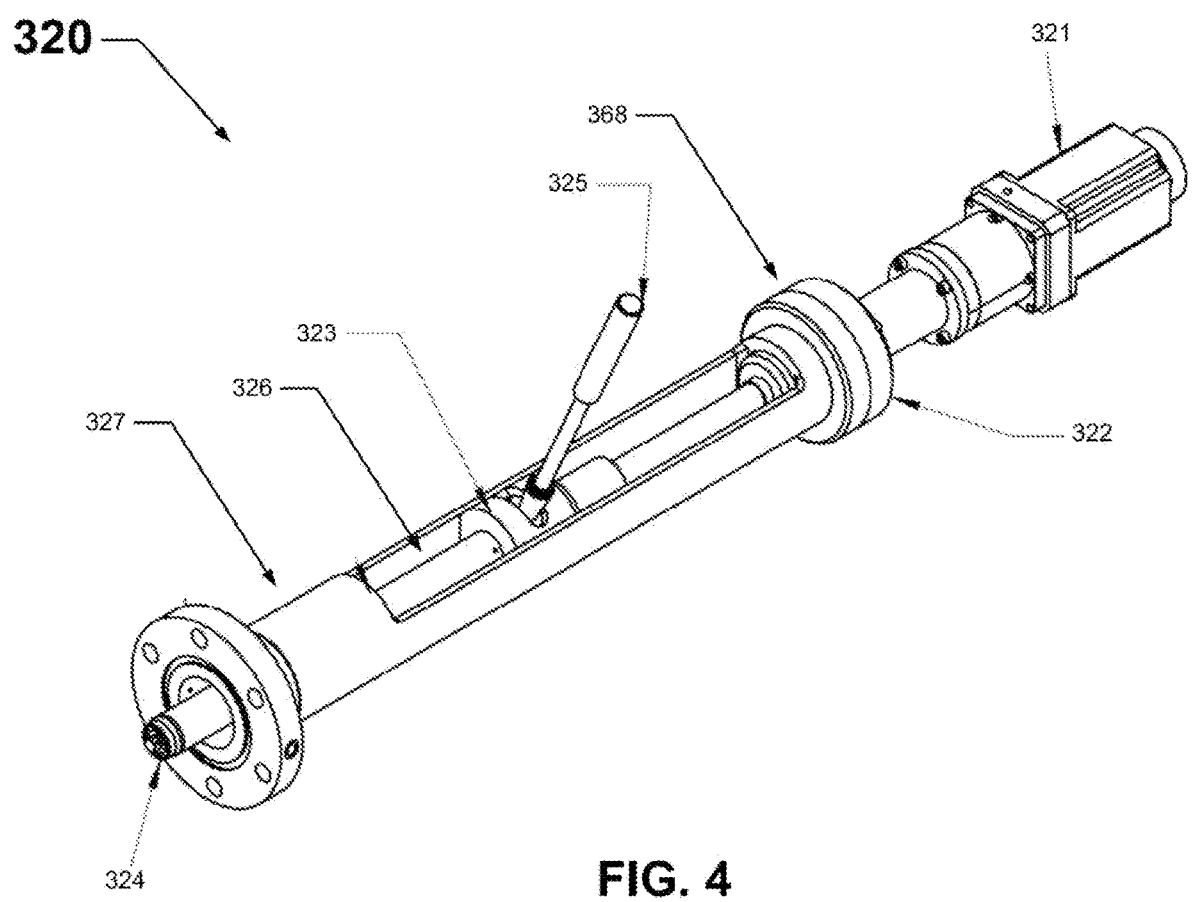
FIG. 4 shows a linear actuator in accordance with certain example embodiments.

FIG. 4 shows a linear actuator 320 in accordance with certain example embodiments. Referring to FIGS. 1 through 4, the linear actuator 320 can include one or more of a number of components having one or more of a number of configurations. For example, in this case, the linear actuator 320 includes a housing 327, an actuator rod 326, a handle 325, a retaining sleeve 323, a plug removal head 324, a torque meter 368 (a type of sensor device 260), a gearmotor mount 322, and a motor 321. As used herein, the term linear actuator should not be used literally. For example, in some alternative embodiments, the actuator can be non-linear. Rather, the linear actuator 320 should be defined for its purpose, which is to facilitate preparing the retrieval vessel 310 and the testing vessel 740 for the transfer of subterranean core samples while maintaining the sampling pressure at which the core samples were taken.

Figure 5A:
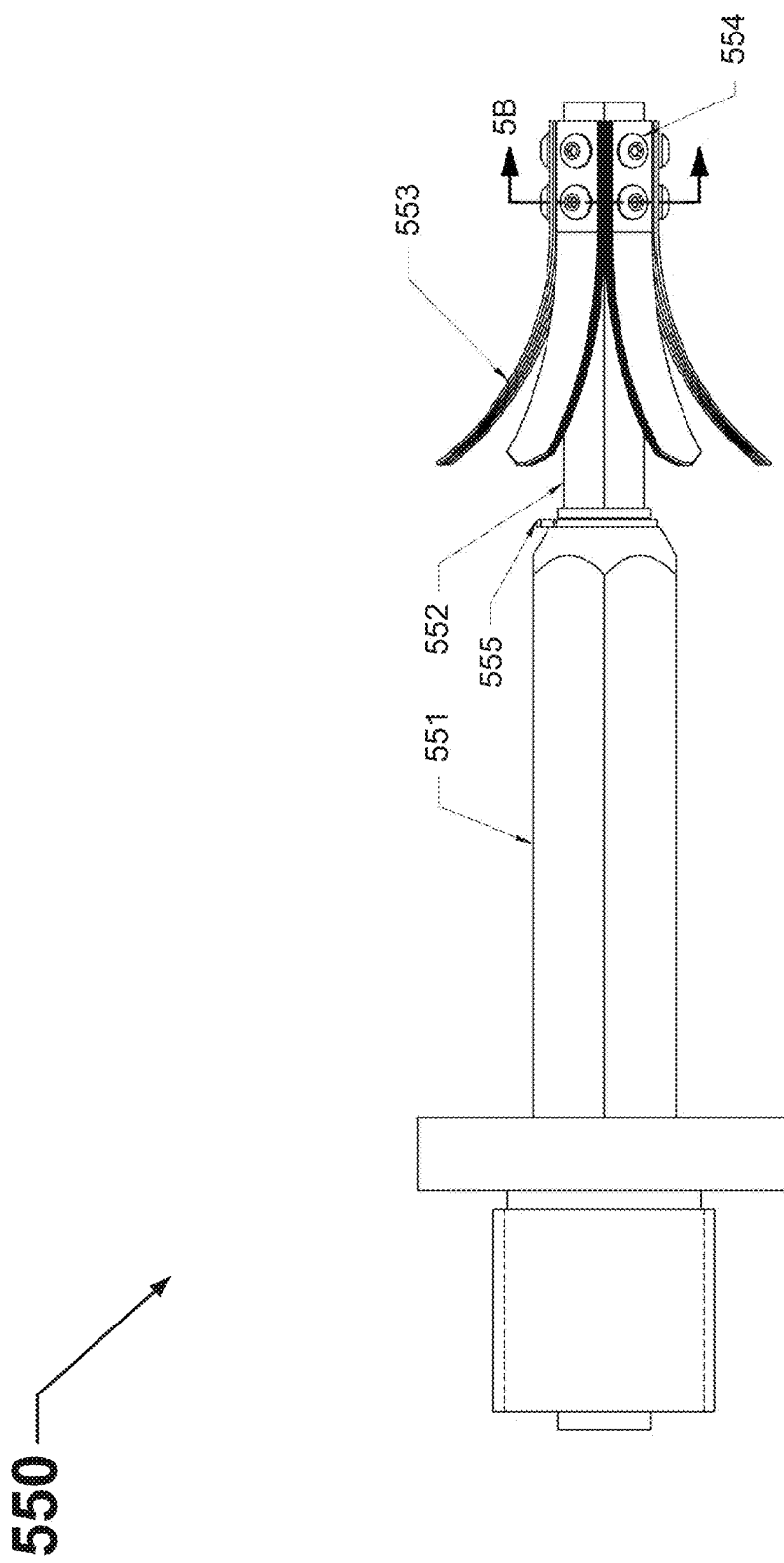
FIGS. 5A through 5C show various views of an extractor in accordance with certain example embodiments.
Figure 5B:
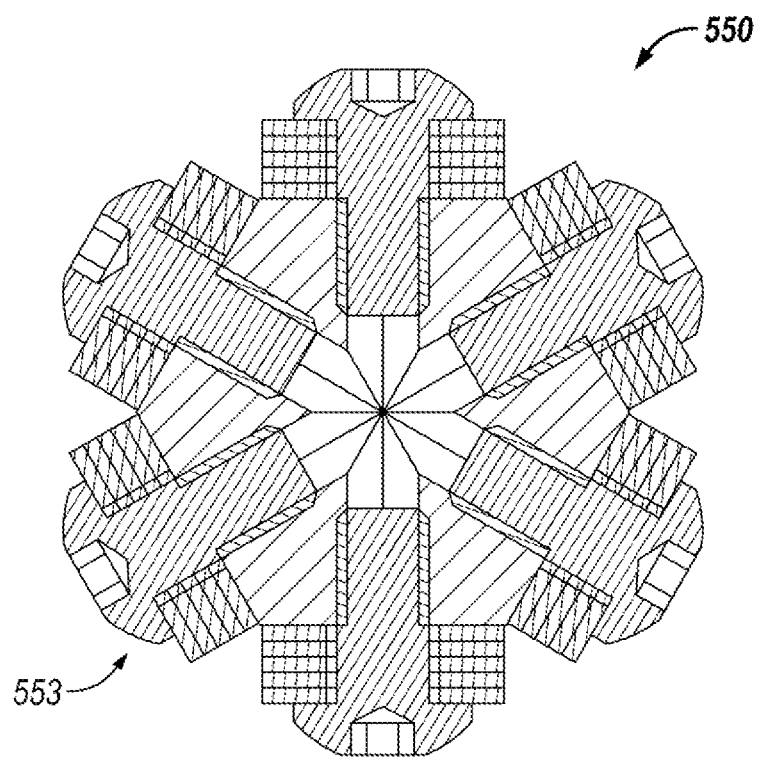
Figure 5C:
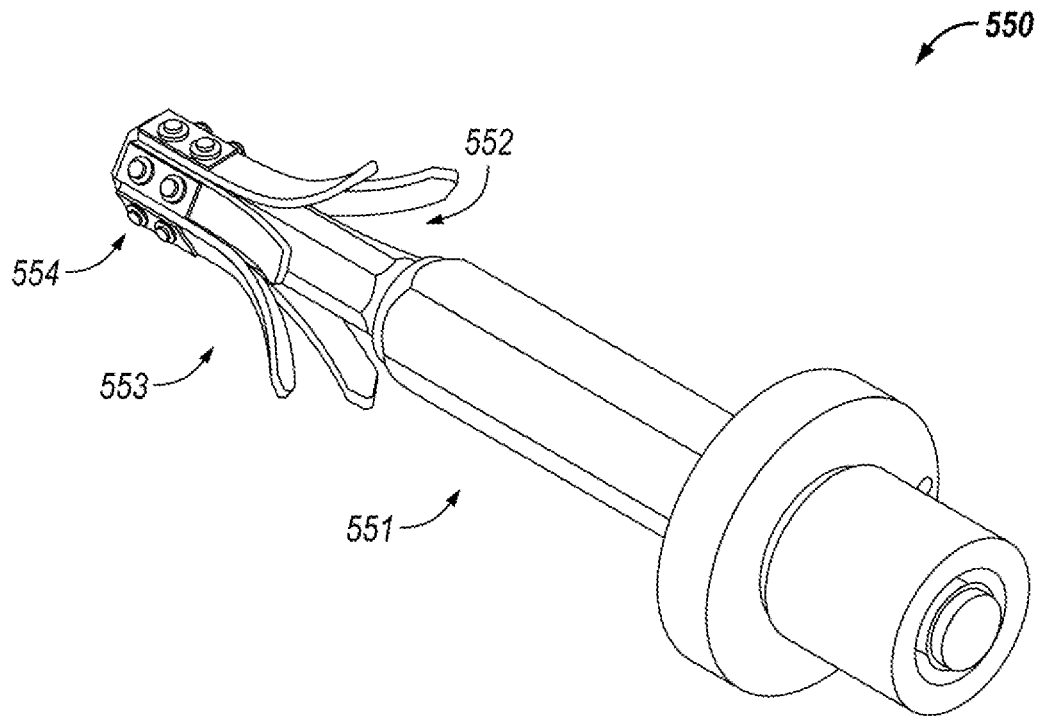

FIGS. 5A through 5C show various views of an extractor 550 in accordance with certain example embodiments. Specifically, FIG. 5A shows a side view of the extractor 550. FIG. 5B shows a front view of the extractor 550. FIG. 5C shows a top-side-rear perspective view of the extractor 550. Referring to FIGS. 1 through 5C, as discussed above, the linear actuator 320 is designed to integrate with one or more ancillary tools, one of which is the extractor 550. For example, the extractor 550 can be used by the linear actuator 320 to extract a spring and plug, both of which are used to maintain the pressure within the retrieval vessel 310. The extractor 550 can include one or more of a number of components having one or more of a number of configurations. For example, in this case, the extractor 550 can include a plug removal head 551, an extractor shaft 552, multiple curved extractor springs 553, multiple fastening devices 554 to secure the curved extractor springs 553 to the extractor shaft 552, and a retaining ring 555. The extractor 550 functions to remove any pressure boundaries and associated components (e.g., threaded plugs, springs) of the retrieval vessel 310 so that access to the core samples for transfer is realized.

Figure 6:
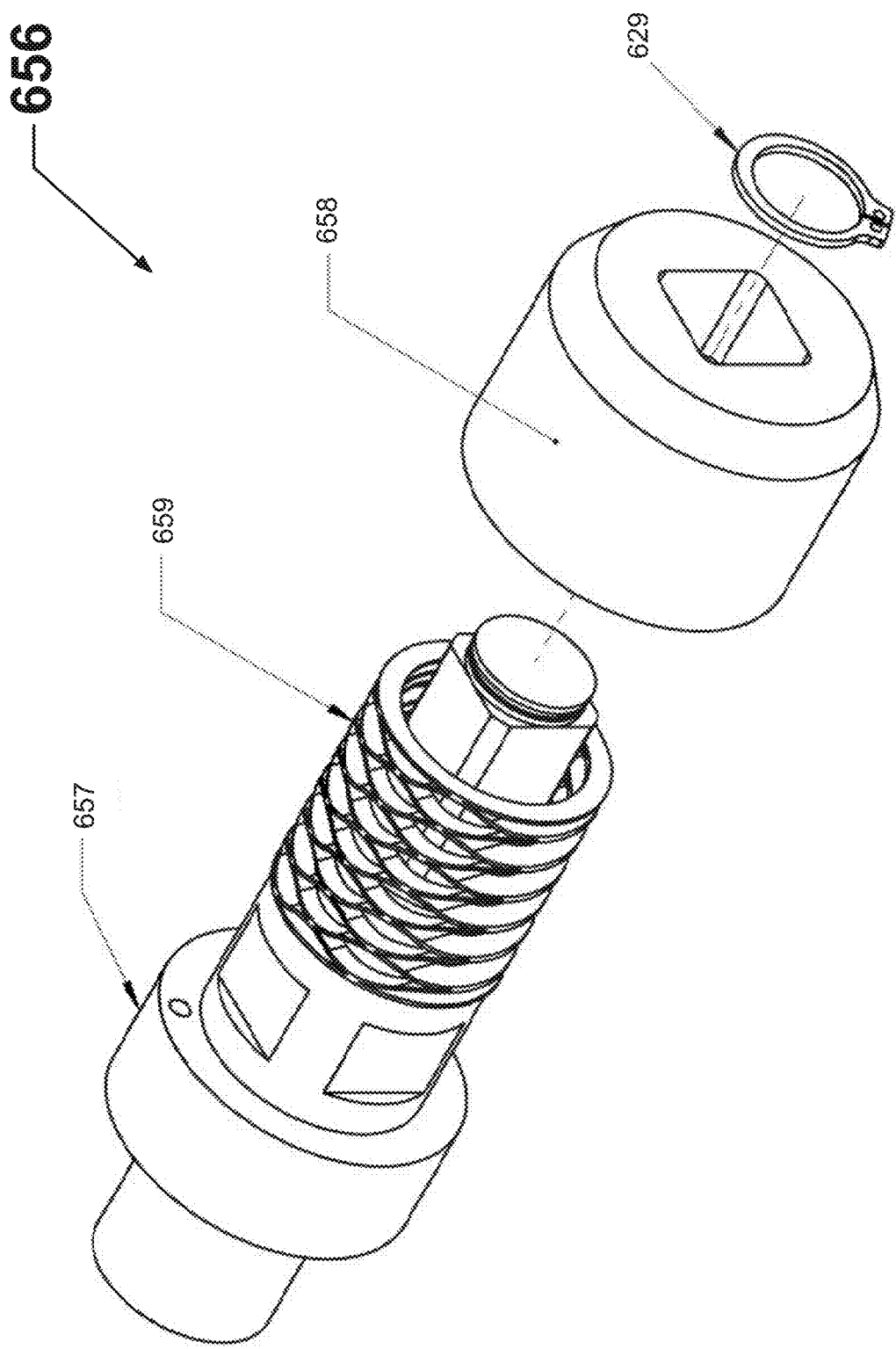
FIG. 6 shows a piston head removal assembly in accordance with certain example embodiments.

FIG. 6 shows a piston head removal assembly 656 in accordance with certain example embodiments. Referring to FIGS. 1 through 6, as discussed above, the linear actuator 320 is designed to integrate with one or more ancillary tools, one of which is the piston head removal assembly 656. For example, the piston head removal assembly 656 can be used by the linear actuator 320 to extract a piston head, which is also used, along with the spring and plug, to maintain the pressure within the retrieval vessel 310. The extractor 550 can include one or more of a number of components having one or more of a number of configurations. For example, in this case, the piston head removal assembly 656 can include a shaft 657, an interface 658, a stacked wave disc spring 659, and a retaining ring 629.

Figure 7A:
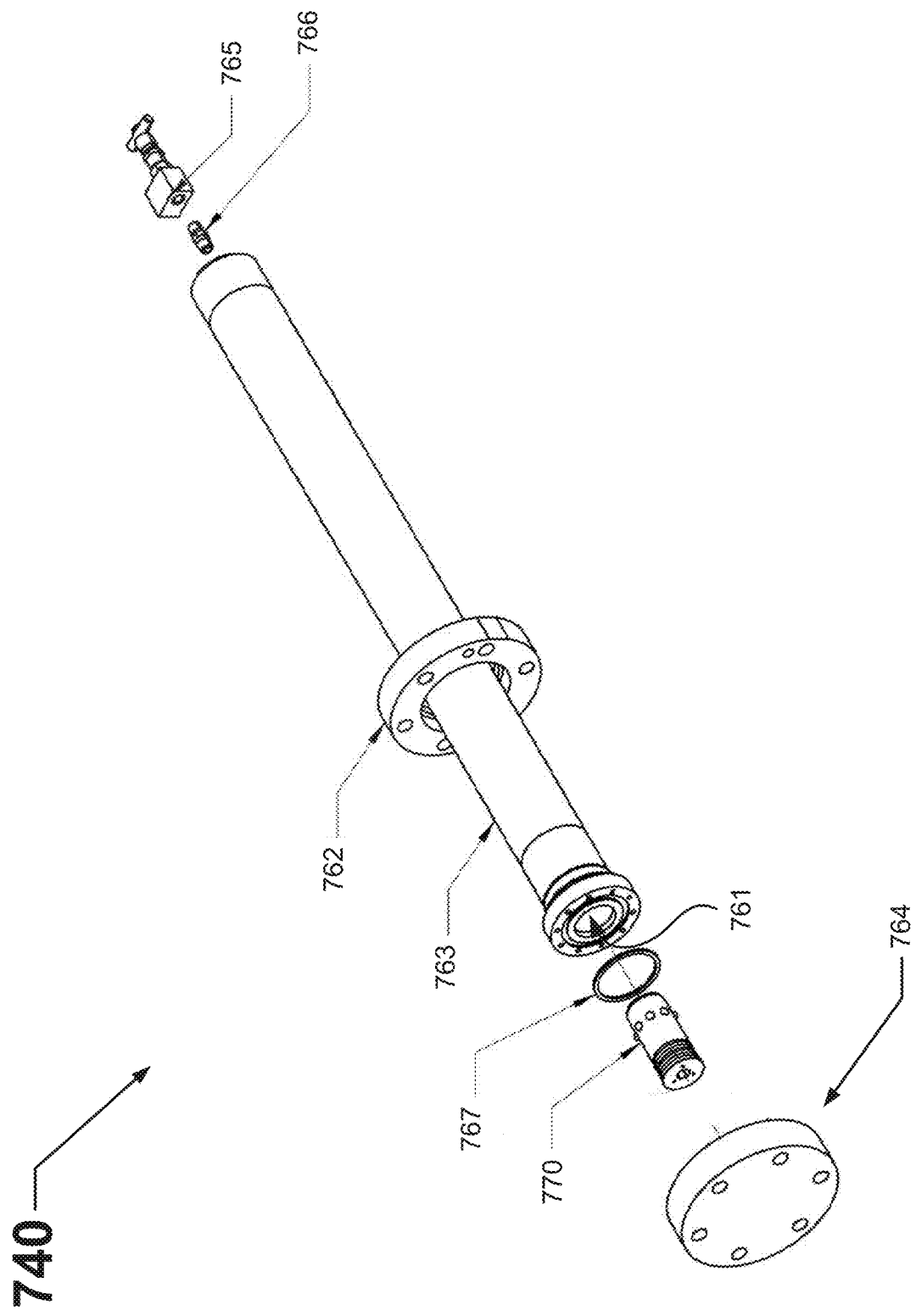
FIGS. 7A through 7D show various views of a testing vessel assembly in accordance with certain example embodiments.
Figure 7B:
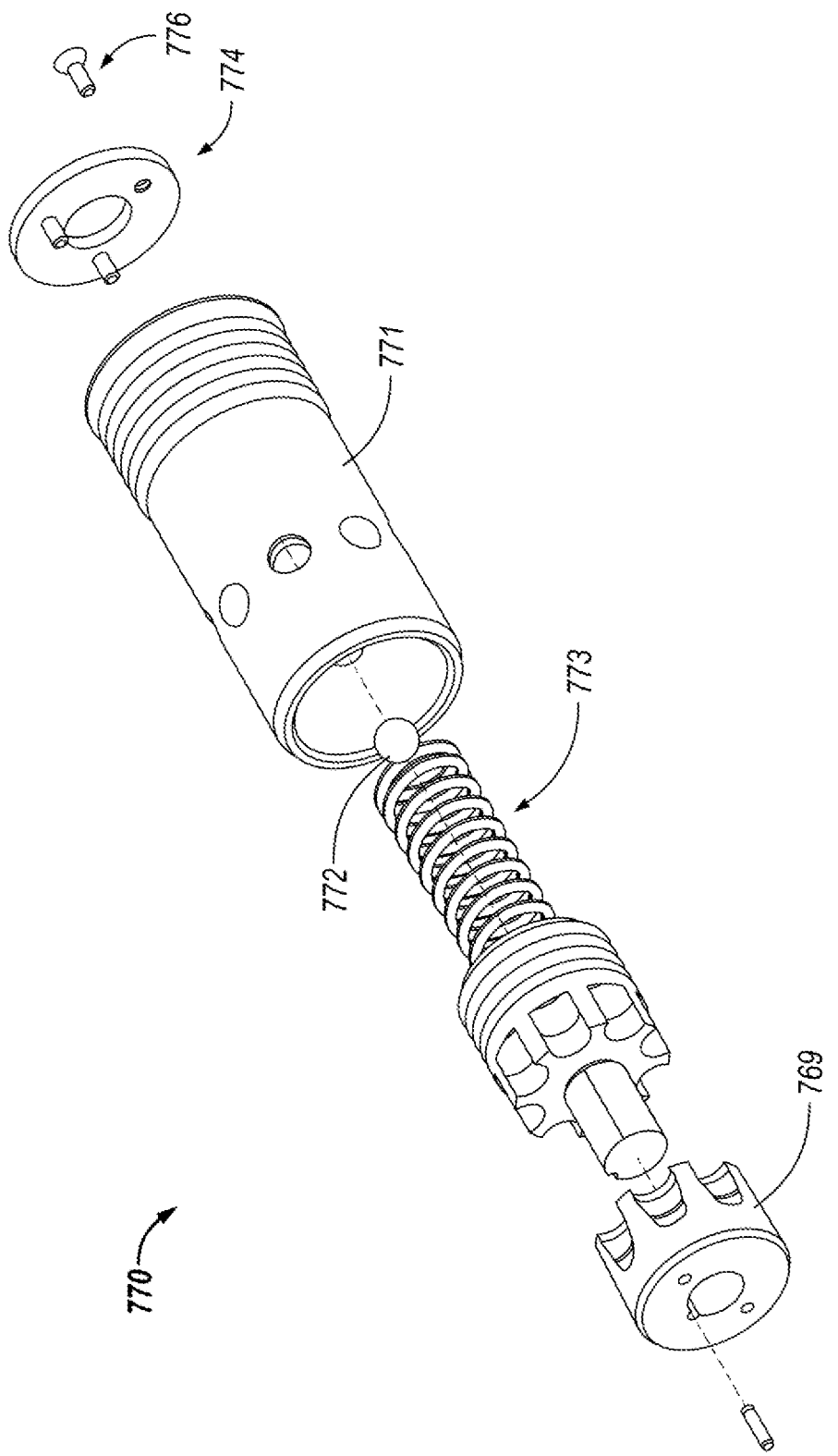
Figure 7C:
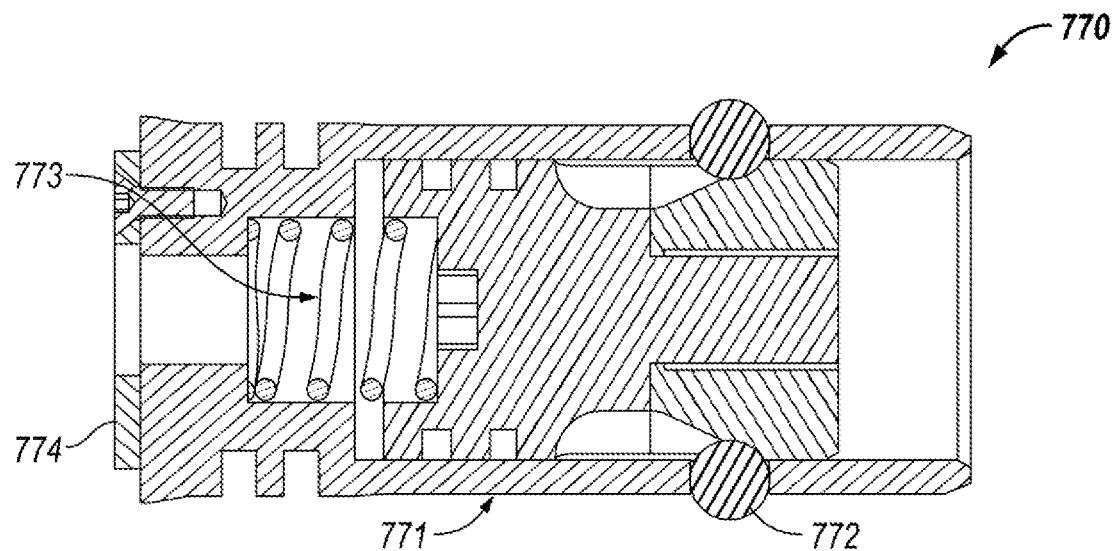
Figure 7D:
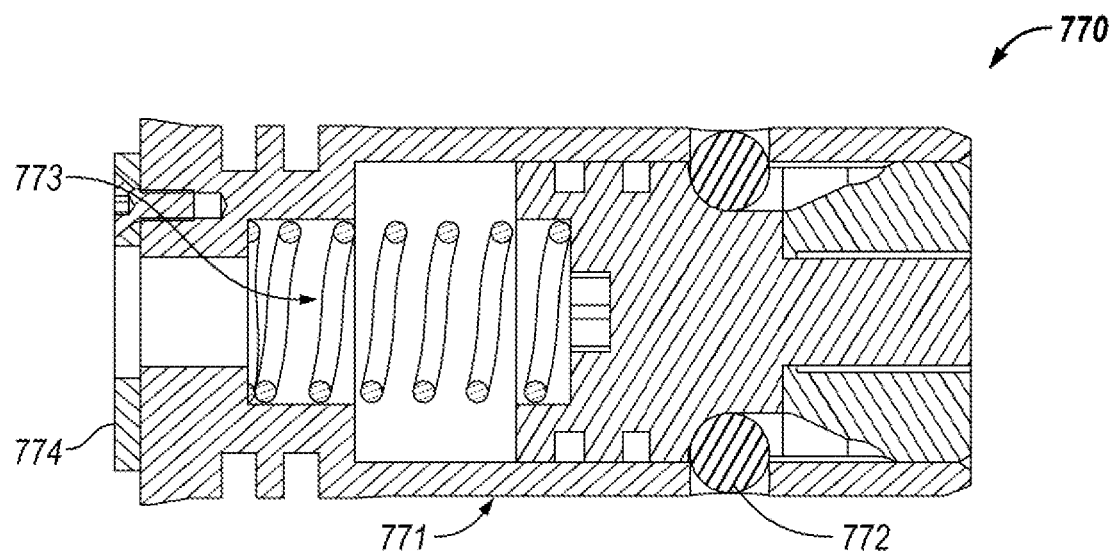

FIGS. 7A through 7D show various views of a testing vessel assembly 740 in accordance with certain example embodiments. Specifically, FIG. 7A shows an exploded isometric view of the testing vessel assembly 740. FIG. 7B shows an exploded isometric view of a testing vessel plug 770 of the testing vessel assembly 740. FIG. 7C shows a cross-sectional side view of the testing vessel plug 770 in a pressurized (closed) condition. FIG. 7D shows a cross-sectional side view of the testing vessel plug 770 in an un-pressurized (open) condition.

Referring to FIGS. 1 through 7D, the testing vessel assembly 740 of FIG. 7A is configured to provide a measurement zone 761 or region within a housing 763 that maintains the subterranean core samples at the sampling pressure while being made of materials (non-magnetic material, non-metallic material) that have a low noise profile when subjected to some of the testing technologies (e.g., NMR, CT) used to test the subterranean core samples. In certain embodiments, the measurement zone 761 defined within the housing 763 of the testing vessel 740 is the region of the testing vessel 740 and the volume contained within that region that may be measured by a test when the testing vessel 740 is appropriately placed in or otherwise subjected to a test instrument.

In certain embodiments, the measurement zone 761 of the testing vessel 740 also includes the region of the testing vessel 740 and the volume contained within that region that may influence a test, for instance, by negatively interfering with the test even when not directly measured when the testing vessel 740 is appropriately placed in or subjected to a test instrument. In certain embodiments, the measurement zone 761 of the testing vessel 740 is the region where the subterranean core samples are housed within testing vessel 740. In certain embodiments, the measurement zone 761 of the testing vessel 740 is the region where the subterranean core samples are housed within testing vessel 740, in addition to about an inch away from the end subterranean core samples. In certain example embodiments, the measurement zone 761 of the testing vessel 740 is the region where the subterranean core samples are housed within the testing vessel 740, in addition to about two inches away from the end subterranean core samples.

The testing vessel assembly 740 can include one or more of a number of components having one or more of a number of configurations. For example, in this case, the testing vessel assembly 740 includes a joint flange 762, the housing 763, the testing vessel plug 770, a blank flange 764, a vent valve 765, a nipple fitting 766, and a face seal 767. The testing vessel assembly 740 can be called by other names, such as a testing vessel 740 and a fiber overwrap vessel assembly 740.

As an example, the testing vessel assembly 740 can use a fiber overwrap design. In such a case, the construction can involve wrapping low/no noise resin and fiber material around a non-metallic/magnetic tube to provide structural integrity. The testing vessel assembly 740 (or at least portions thereof that form the measurement zone 761) is designed for low/no noise while able to maintain the same or higher pressure present in the retrieval vessel. As another example, the testing vessel assembly 740 can use a low/no noise glass/thermoplastic composite to construct the measurement zone 761 of the testing vessel assembly 740.

As used herein, no noise materials may refer to materials that give no signal in a test performed on the testing vessel assembly 740. Further, low noise materials may refer to materials that give an acceptably small signal in a test performed on the testing vessel assembly 740, that do not interfere with or otherwise obscure the signal given in the test by the core samples contained in the measurement zone 761 of the testing vessel assembly 740.

The testing vessel assembly 740 can include metallic flanged ends structurally integrated into the non-metallic center portion (e.g., the measurement zone 761) of the testing vessel assembly 740. The metallic ends facilitate incorporation of flanges for attachment to the valve 335 and also facilitate threading for pressure fittings and fasteners. In some cases, the flanged end caps are made of titanium (e.g., non-ferrous, non-magnetic metal).

Similarly, the testing vessel plug 770 of the testing vessel 740 is configured to, when used with the housing 928 of FIGS. 9A and 9B below, plug and seal the cavity of the testing vessel 740 to maintain a pressure (e.g., a sampling pressure) within the testing vessel 740. The core samples in the measurement zone 761 of the testing vessel 740 are maintained at a substantially equivalent pressure or placed under a higher pressure during the transfer of the one or more subterranean core sample from the retrieval vessel 310 to the testing vessel 740. By doing so, the testing and corresponding test results on the subterranean core samples can be more accurate (e.g., more representative of reservoir conditions). For example, embodiments consistent with the present disclosure may be utilized for characterizing the subterranean core samples and their fluid contents, both while at the initial received pressure (called the sampling pressure herein) and during the depressurization process. Furthermore, embodiments consistent with the present disclosure may be utilized for characterizing subterranean core samples that have been recovered and maintained at elevated pressure and/or temperature.

In certain embodiments, the subterranean core samples have been maintained at the original reservoir pressure (sampling pressure) and/or temperature, so that there are minimal or no structural changes to the subterranean core samples, and/or minimal or no changes to the composition and/or phase of the fluids contained in the subterranean core samples. In certain example embodiments, representative conditions may refer to when the subterranean core samples have been maintained at an elevated pressure and/or temperature that is/are representative of the original reservoir pressure and/or temperature, such that the fluids contained in the subterranean core samples have not undergone a phase transition (e.g., at a bubble point or dew point) and the fluid contents of the subterranean core samples remain representative of reservoir conditions.

Additionally, in certain embodiments, representative conditions may refer to the structure of the subterranean core samples having changed less than if the pressure and/or temperature had been allowed to reach ambient conditions. The testing vessel plug 770 can include one or more of a number of components having one or more of a number of configurations. For example, in this case, the testing vessel plug 770 includes a plug piston assembly 769, a housing 771, multiple retaining balls 772, a compression spring 773, an attachment ring 774, and multiple fastening devices 776 (e.g., screws).

The testing vessel plug 770 is designed so that it incorporates no threaded interfaces as to keep the inner bore of the testing vessel 740 as smooth and obstruction free as possible. A smooth bore increases the likelihood that the core samples will be transferred unencumbered by any irregular bore features. The testing vessel plug 770 functions on the principal of differential pressure, whereby once the testing vessel plug 770 is in place and external pressure is released, the resulting differential pressure shifts the plug piston assembly 769. The shift in the plug piston assembly 769 causes the retaining balls 772 to be forced radially outward into a corresponding retaining feature (groove) on the inner surface of the housing 763 where they are secured and able to react the internal pressure loading.

The testing vessel plug 770 is removed by releasing the internal pressure of the testing vessel 740, thereby eliminating the differential pressure bias. The compression spring 773 returns the piston of the plug piston assembly 769 to an inactive state. FIGS. 7C and 7D depict the articulation of the testing vessel plug 770 where FIG. 7C depicts an activated plug with an internally biased pressure differential and 7D is shown inactivated with no pressure bias. Internal pressure is referenced as to the right of the testing vessel plug 770 depicted on FIGS. 7C and 7D and is external to the left with sealing grooves depicted in the center of the outer diameter of the testing vessel plug 770.

Figure 8A:
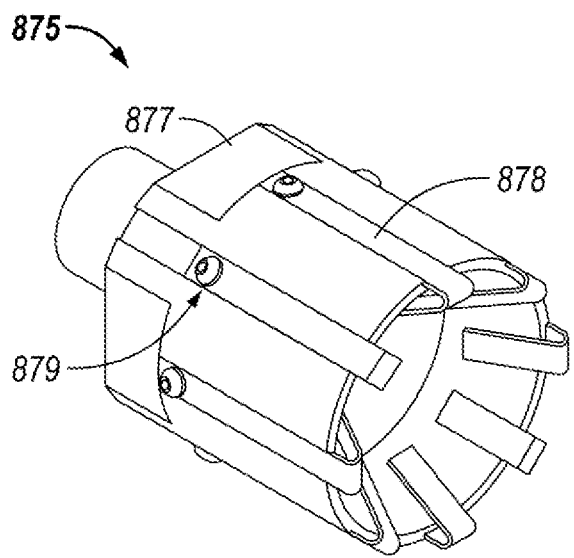
FIGS. 8A through 8C show various views of a spring extractor assembly in accordance with certain example embodiments.
Figure 8B:
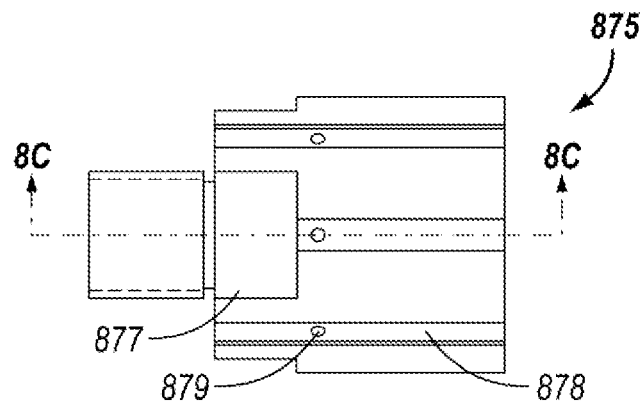
Figure 8C:
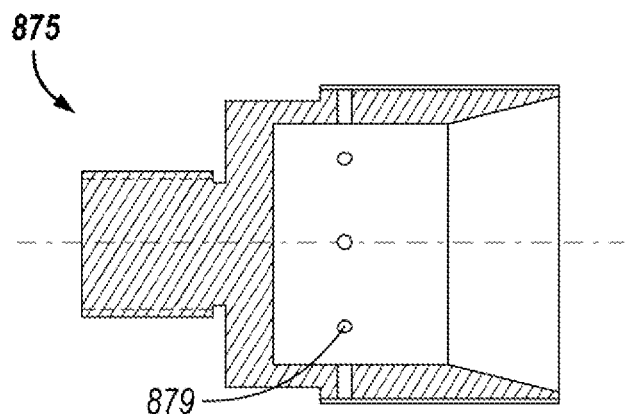

FIGS. 8A through 8C show various views of a spring extractor assembly 875 in accordance with certain example embodiments. Specifically, FIG. 8A shows an isometric perspective view of the spring extractor assembly 875. FIG. 8B shows a side view of the spring extractor assembly 875. FIG. 8C shows a cross-sectional side view of the spring extractor assembly 875. Referring to FIGS. 1 through 8C, as discussed above, the linear actuator 320 is designed to integrate with one or more ancillary tools, one of which is the spring extractor assembly 875. For example, the spring extractor assembly 875 is a device that can be used as a substitute for part of the extractor 550 for removing the spring within the retrieval vessel 310. The spring extractor assembly 875 can include one or more of a number of components having one or more of a number of configurations. For example, in this case, the spring extractor assembly 875 includes multiple spring remover heads 877 that each covers a bottom part of some of the leaf extractor springs 878, and where each leaf extractor spring 878 is secured to a housing by a fastening device 879 (e.g., a screw). The spring extractor assembly 875 is designed to be inserted over a compression spring that can be an integral component of the retrieval vessel. Leaf extractor springs 878 deflect as they are inserted over the compression spring, allowing insertion, however hook into and hold onto the spring during retraction/removal.

Figure 9A:
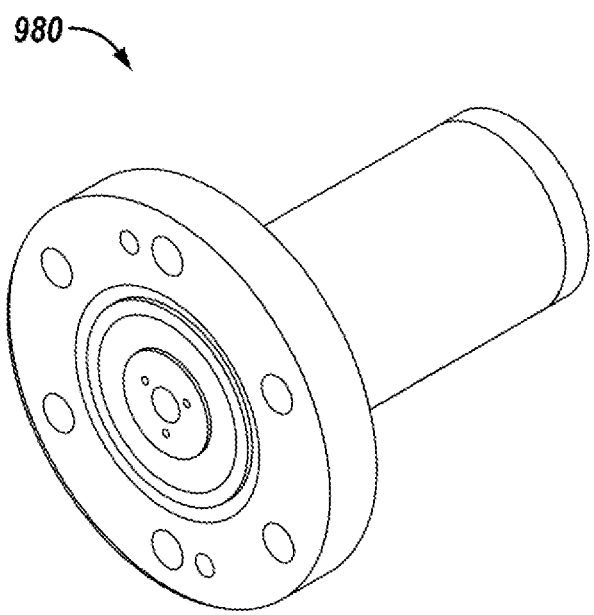
FIGS. 9A and 9B show various views of a testing vessel plug assembly in accordance with certain example embodiments.
Figure 9B:
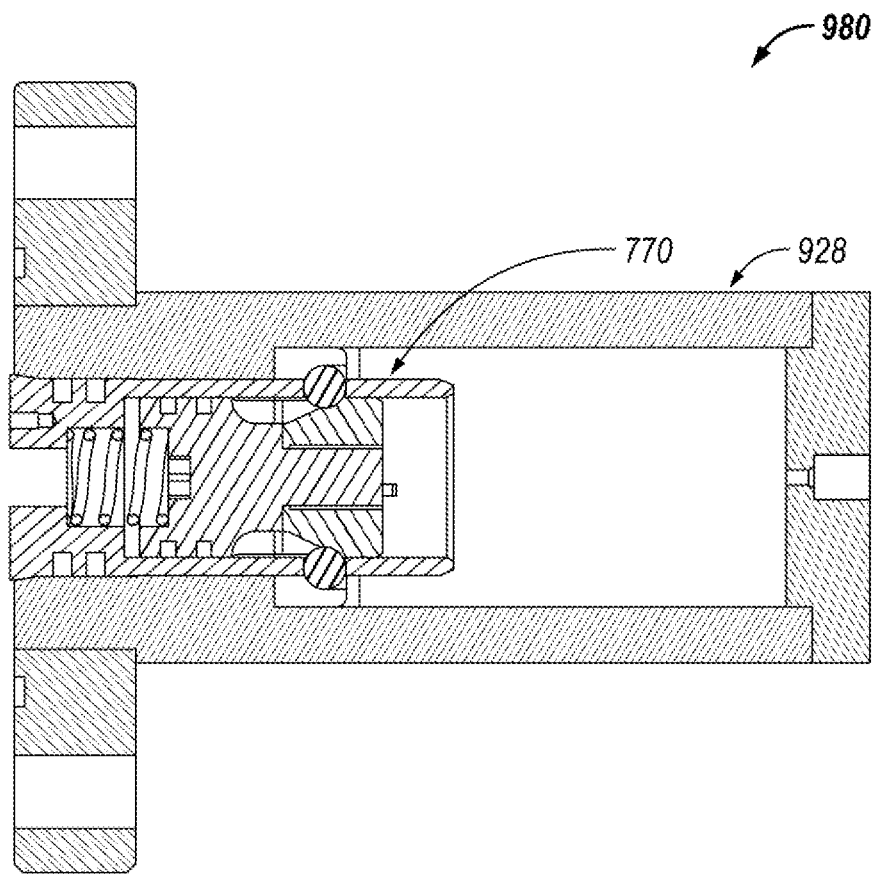

FIGS. 9A and 9B show various views of a testing vessel plug assembly 980 in accordance with certain example embodiments. Specifically, FIG. 9A shows an isometric perspective view of the testing vessel plug assembly 980. FIG. 9B shows a cross-sectional side view of the testing vessel plug assembly 980. Referring to FIGS. 1 through 9B, the testing vessel plug assembly 980 is configured to plug and seal the cavity of the testing vessel 740 to maintain a pressure (e.g., a sampling pressure) within the testing vessel 740. The testing vessel plug assembly 980 can include one or more of a number of components having one or more of a number of configurations. For example, in this case, the testing vessel plug assembly 980 includes the testing vessel plug 770 disposed in a housing 928.

Figure 10A:
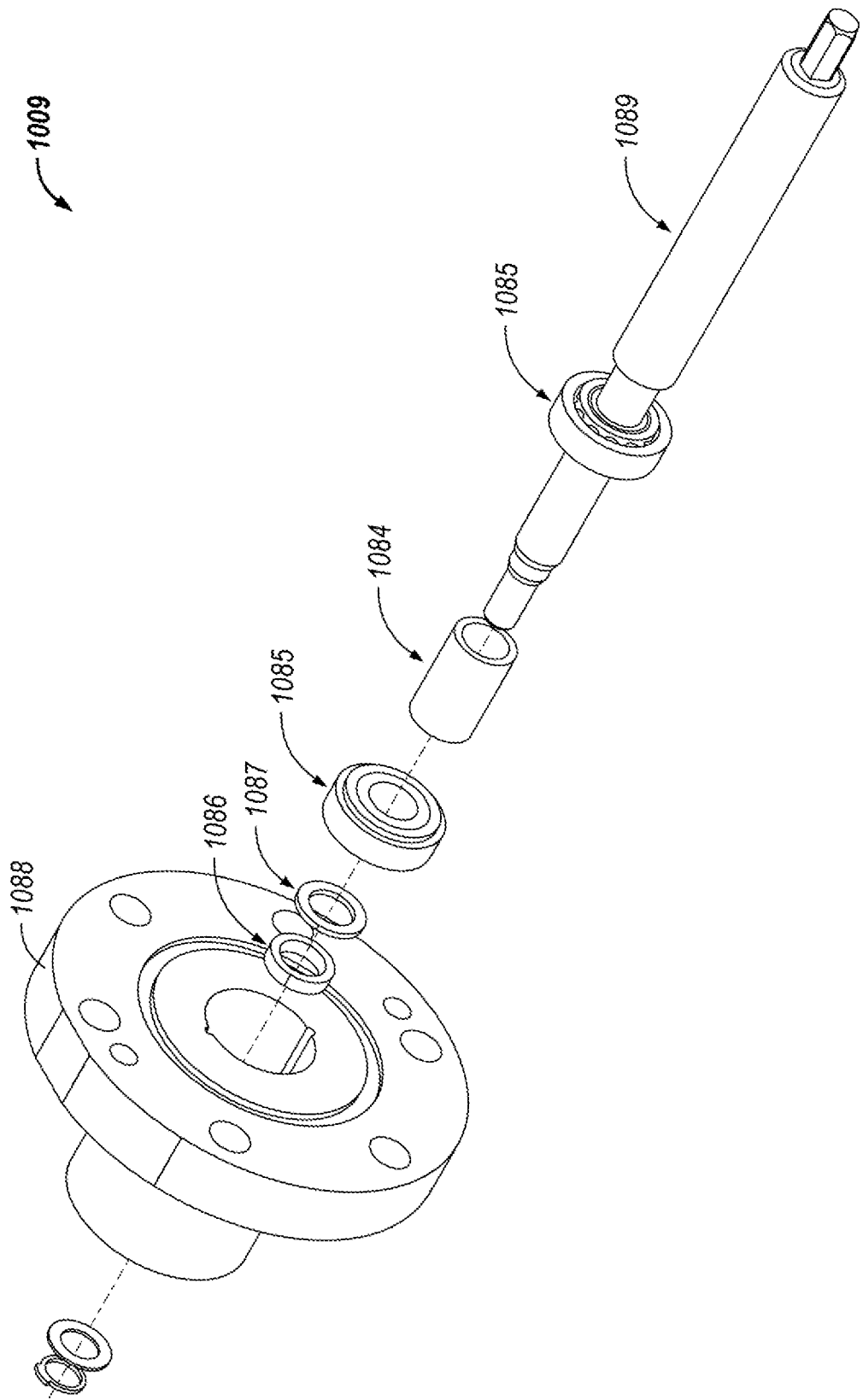
FIGS. 10A and 10B show various views of a plug breaker assembly in accordance with certain example embodiments.
Figure 10B:
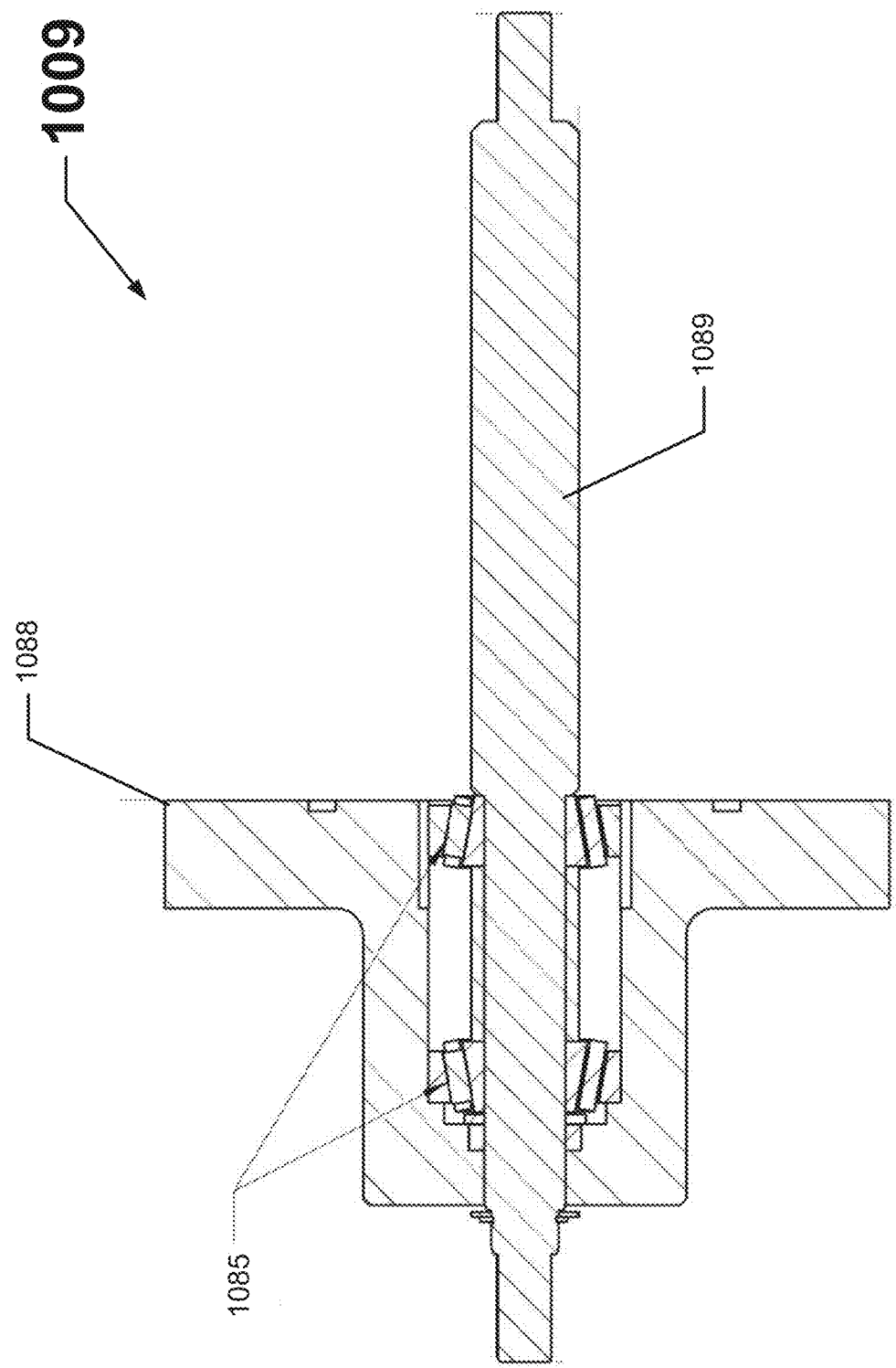

FIGS. 10A and 10B show various views of a plug breaker assembly 1009 in accordance with certain example embodiments. Specifically, FIG. 10A shows a bottom-side-top perspective view of the plug breaker assembly 1009. FIG. 9B shows a cross-sectional side view of the plug breaker assembly 1009. Referring to FIGS. 1 through 10B, the plug breaker assembly 1009 is configured to break down and/or remove at least one of the pressure barrier components within the retrieval vessel (e.g., retrieval vessel 310). The plug breaker assembly 1009 is able to apply higher torque loads than the linear actuator 320 to remove higher preloaded threaded pressure barriers such as large threaded plugs. The plug breaker assembly 1009 can include one or more of a number of components having one or more of a number of configurations. For example, in this case, the plug breaker assembly 1009 includes a flange 1088, a shaft 1088, a sleeve 1084, two tapered roller bearings 1085, a rotary seal 1086, and brass shim 1087.

Figure 11:
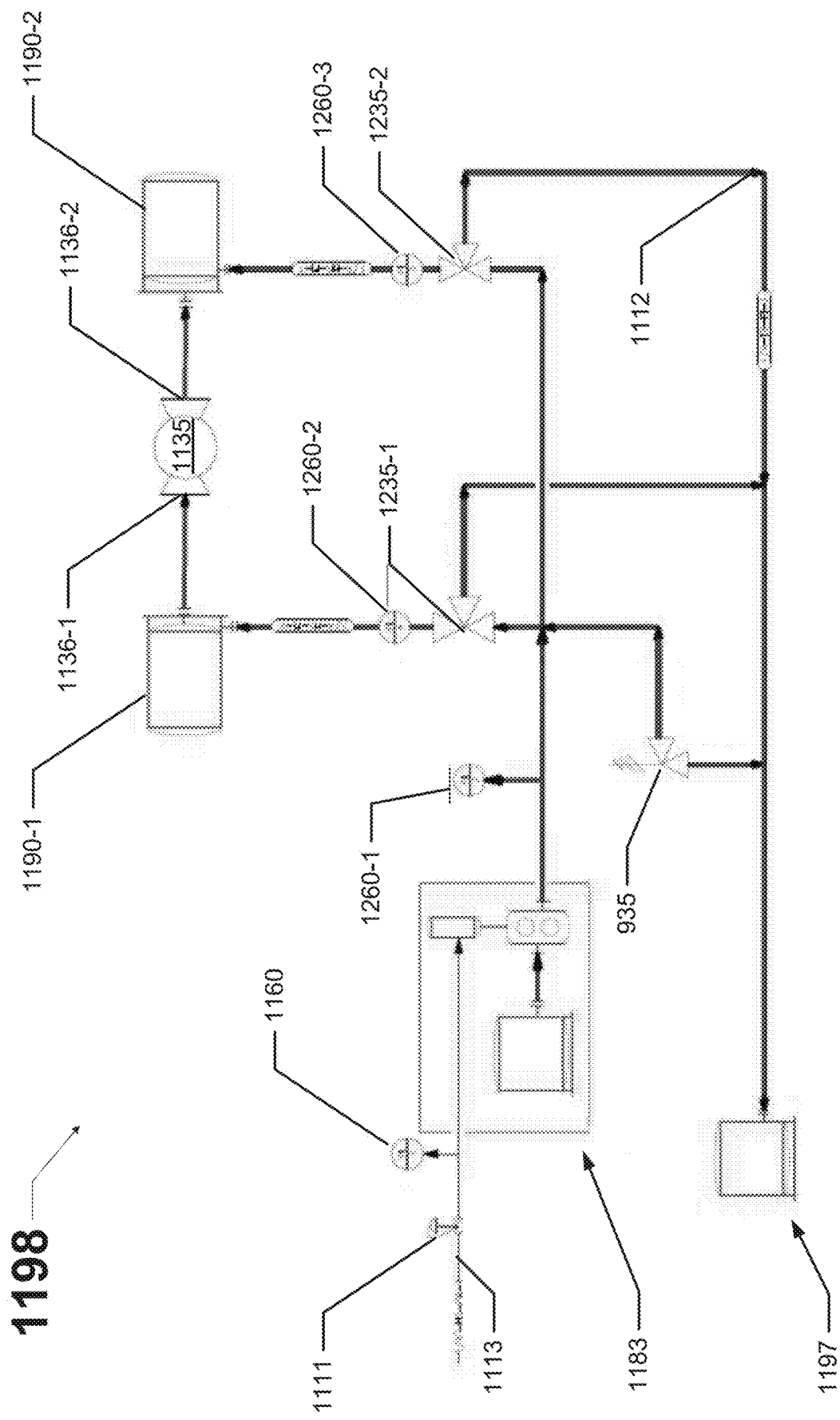
FIG. 11 shows a schematic of a tool system in accordance with certain example embodiments.
Figure 12A:
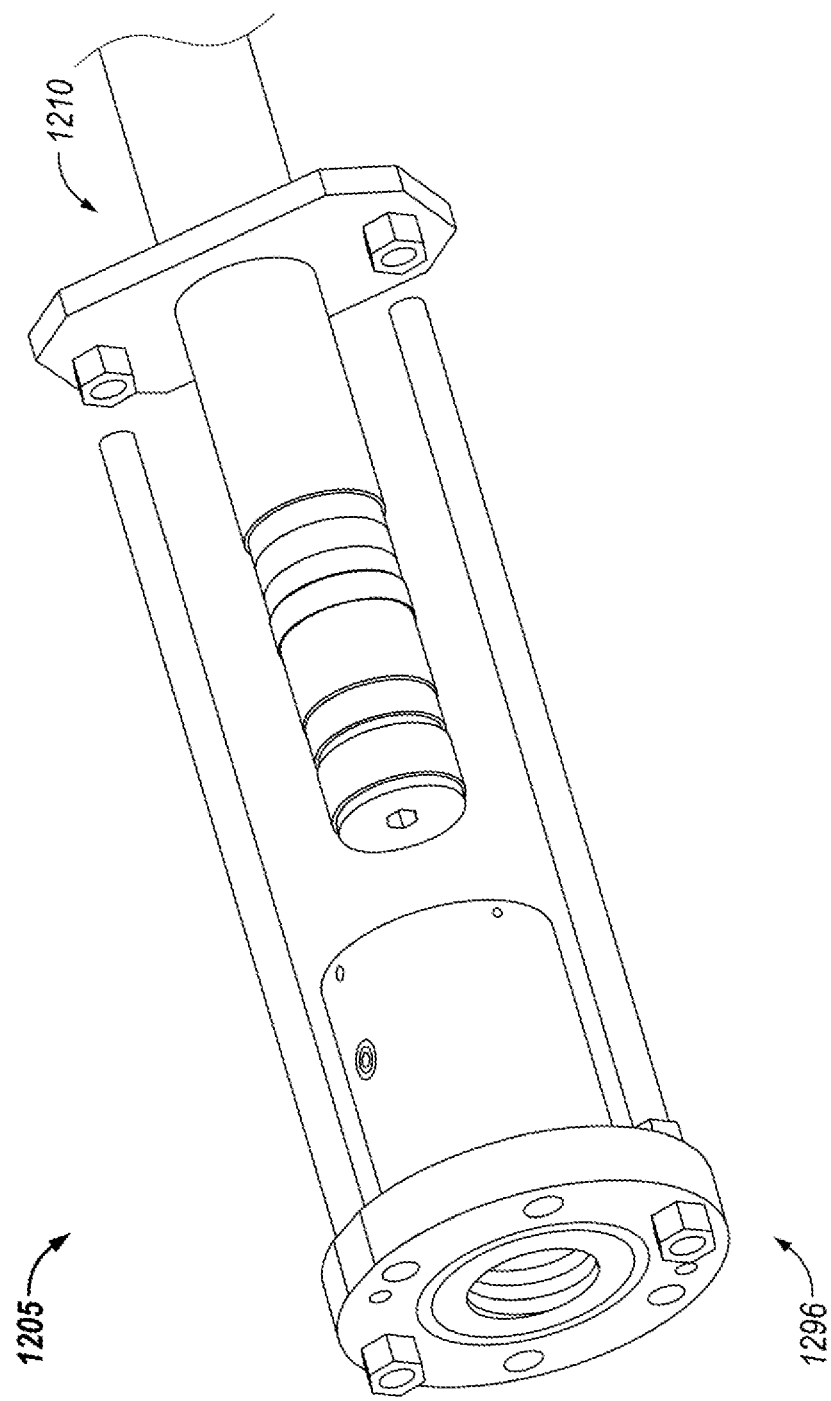
Figure 12B:
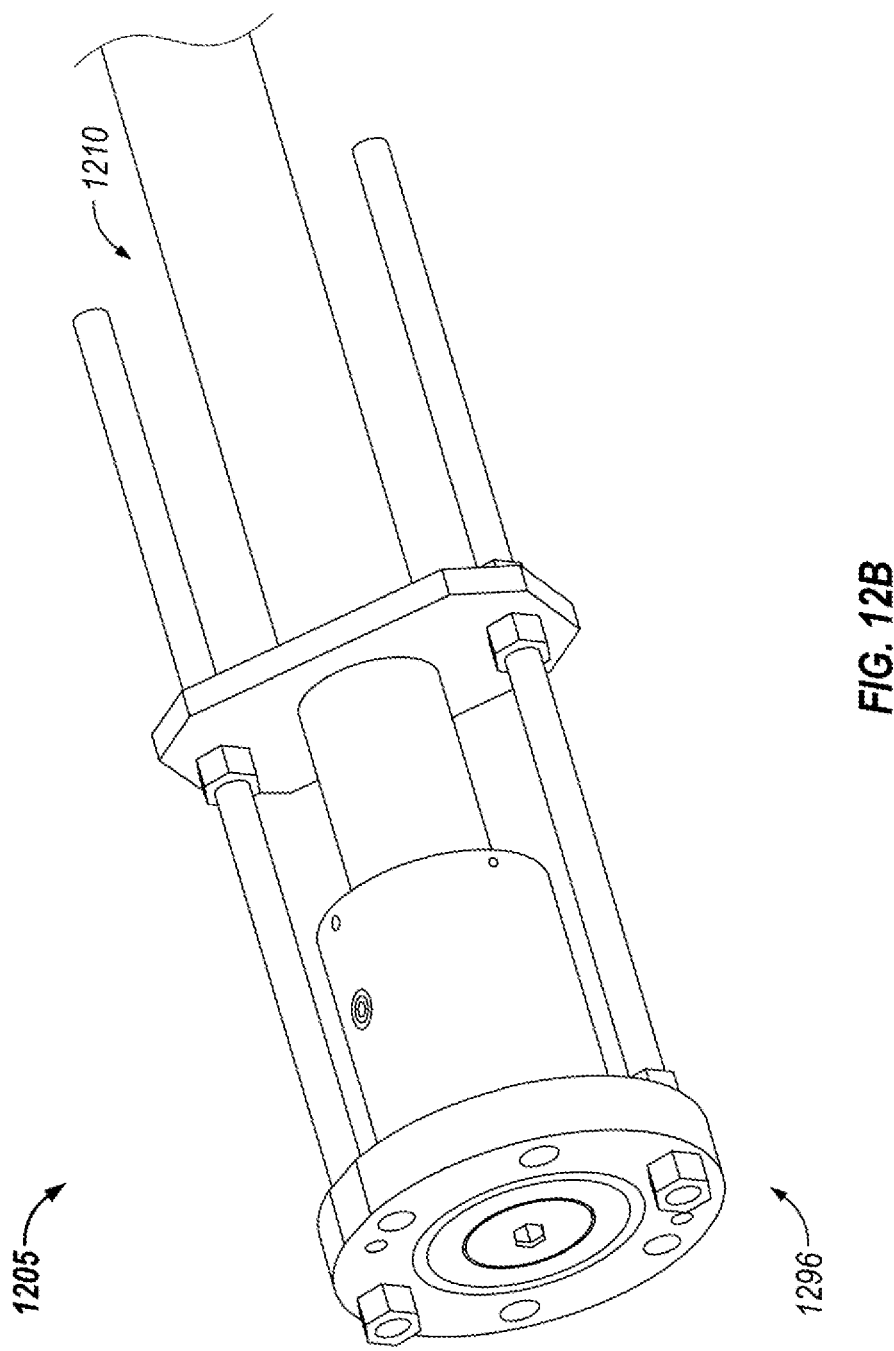

FIG. 11 shows a schematic piping and instrumentation diagram drawing 1198 of a tool system in accordance with certain example embodiments. Referring to FIGS. 1 through 11, the schematic drawing 1198 shows the piping configuration of an example tool system. The various parts (e.g., the valve 1135, the components 1190, the hydraulic device 1183) of the schematic drawing 1198 of FIG. 11 are substantially the same as the corresponding parts of the figures discussed above. In this case, piping 1113 feeds air through a regulator 1111 and measured by a sensor device 1160 in the form of a pressure gauge to part of the hydraulic device 1183, which in this case is an air-driven hydraulic pump. The hydraulic device 1183 outputs pressurized fluid (e.g., fluorinert up to 6000 psi) through a number of hydraulics lines 1112 as measured by a sensor devices 1260-1, 1260-2, and 1260-3 each in the form of a pressure gauge.

The pressurized fluid from the hydraulic device 1183 is distributed to component 1190-1 through a valve 1235-1 in the form of a three-way valve when the valve 1235-1 is open and to an excess fluid catch tank 1197 when the valve 1235-1 is closed. Simultaneously, the pressurized fluid from the hydraulic device 1183 is distributed to component 1190-2 through a valve 1235-2 in the form of a three-way valve when the valve 1235-2 is open and to the excess fluid catch tank 1197 when the valve 1235-2 is closed. The fluid flowing through the open valve 1235-1 to component 1190-1 is measured by sensor device 1260-2 in the form of a pressure gauge, and the fluid flowing through the open valve 1235-2 to component 1190-2 is measured by sensor device 1260-3 in the form of a pressure gauge.

Components 1190-1 and 1190-2 are equivalent to components 290-1 and 290-2 of FIG. 2. Similarly, valve 1135 of FIG. 11 is equivalent to valve 235 of FIG. 2. As the case with FIG. 2, the valve 1135 is mechanically and detachably coupled to component 1190-1 using coupling feature 1136-1 and to component 1190-2 using coupling feature 1136-2. Valve 1135 in this case is a ball valve. There is also a valve 935 in the form of a pressure relief integrated with the hydraulic lines 1112 between the output of the hydraulic device 1183 and the excess fluid catch tank 1197.

FIGS. 12A through 21 show various stages for transferring pressurized reservoir core samples in accordance with certain example embodiments. Referring to FIGS. 1 through 21, FIGS. 12A and 12B show a step 1205 in the process where an adapter flange 1296 is installed on the end of the retrieval vessel 1210. Prior to this point in time (prior to step 1205), the retrieval vessel 1210 (also sometimes called a core vault) is removed from a BHA or general core retrieval tool. Tests should be performed to ensure that the subterranean core samples are still pressurized and/or to determine the level of pressurization required to transfer the core samples to the testing vessel 740. Any devices of FIGS. 12A through 21 can be substantially the same as the corresponding devices of FIGS. 1 through 11.

In step 1205, the adapter flange 1296 is placed about the end (e.g., the pressure tube) of the retrieval vessel 1210. Moderate resistance can be caused by the seal compression. When enough axial force is applied to compress the initial radial seal, the screw threads of the two long screws can be engaged. After the threads of the screws of the adapter flange 1296 have engaged, the retrieval vessel 1210 can be rotated/threaded and fully seated in position within the adapter flange 1296. The fully seated position can be verified when the cap of the retrieval vessel 1210 is recessed by a certain amount from the face of the adapter flange 1296. To secure the adapter flange 1296 to the retrieval vessel 1210, a number of set screws can be provided and torqued to a certain amount. In some cases, a user may mark a reference line on the tube/flange interface of the retrieval vessel 1210 to visually indicate any relative movement during the process.

In step 1305, shown in FIG. 13 and some period of time after step 1205, hydraulic lines are installed to access and equalize to the internal pressure of the retrieval vessel 1210. Here, the retrieval vessel 1210 is coupled to the valve 1335 of the valve assembly 1330 using coupling features 1336 of the valve 1335 (in this case, a ball valve) and coupling features 1291 of the retrieval vessel 1210. The valve assembly is mounted on a frame 1395. The combined retrieval vessel 1210 and adapter flange 1296 is connected to the valve 1335 using bolts (or other fastening devices), which act as the coupling features 1336 of the valve 1335. A high pressure line is then connected to the lower port of the adapter flange (not shown in FIG. 13).

A user can then vent the upper port 1306 and pressurize the retrieval vessel 1210, adapter flange 1296, and valve 1335 with a hydraulic device (e.g., hydraulic device 1183 in the form of an air driven pump) until fluid trickles from the upper port, which removes all air from the internal adapter flange. At that point, a user can close the upper port and pressurize the combined volume to match the internal volume of the retrieval vessel 1210 using the hydraulic device and one or more valves (e.g., pressure relief valve 935 of FIG. 11). Using a tool (e.g., a long reach allen wrench) that extends through the open valve 1335, the tool can be used to open the access valve hex located on the retrieval vessel 1210. For example, by rotating the access valve hex counterclockwise 1-1.5 full turns, the access valve hex will open. Once open, the pressures will equalize, thereby gaining access to the internal pressure of the core chamber of the retrieval vessel 1210 while a hydraulic device (e.g., hydraulic device 1183) maintains pressure. FIG. 13 also shows at least 2 pressure ports 1306.

Figure 14:
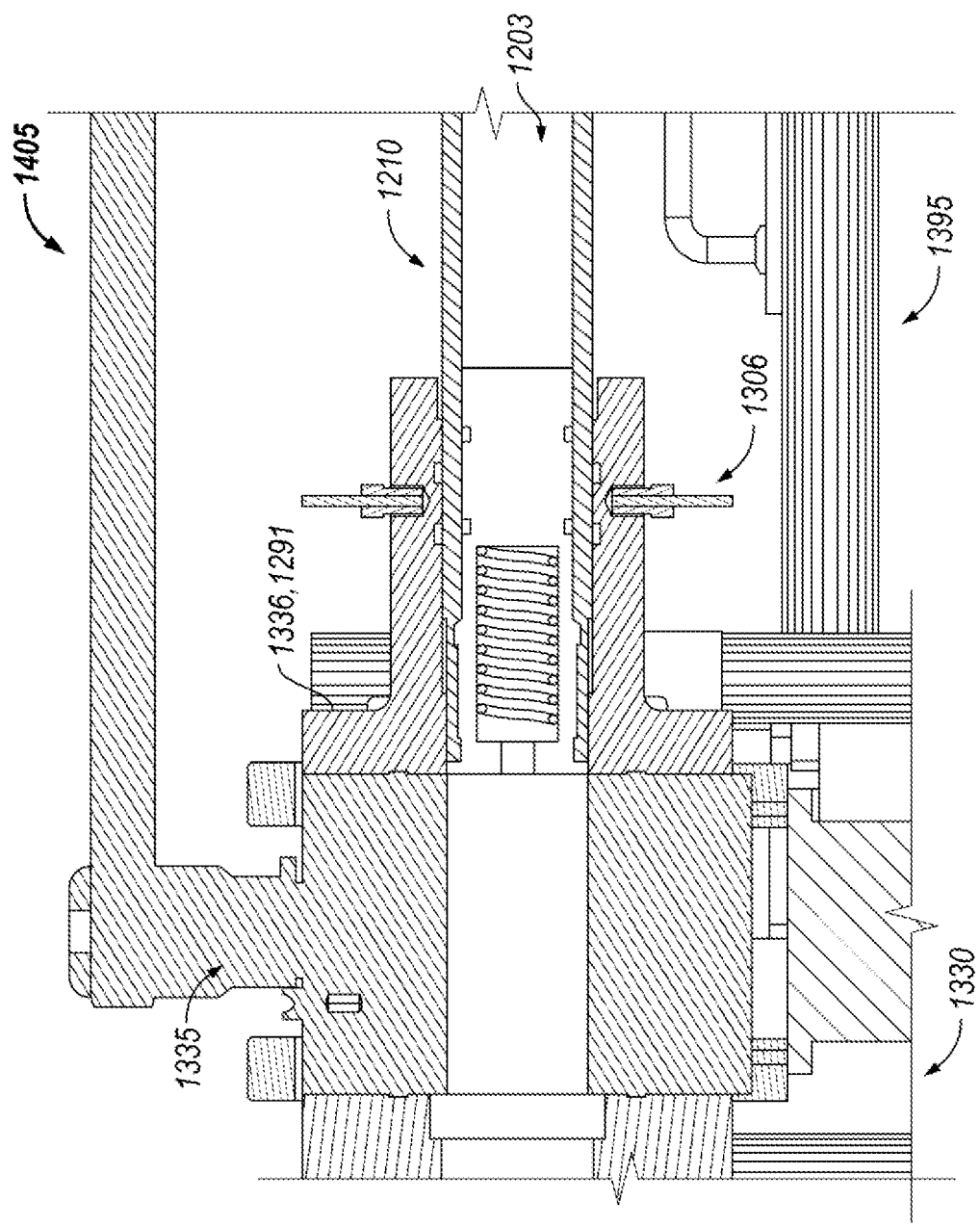

In step 1405, shown in FIG. 14, a view is provided as to the three pressure barrier components (spring, plug, and piston head) within the retrieval vessel 1210. As in FIG. 13, the combined retrieval vessel 1210 and adapter flange 1296 is connected to the valve 1335 of the valve assembly 1330 using bolts (or other fastening devices), which are disposed in the coupling features 1336 of the valve 1335 and the coupling features 1291 of the retrieval vessel 1210. Some of the core samples 1203 are shown within the retrieval vessel 1210 in FIG. 14.

Figure 15:
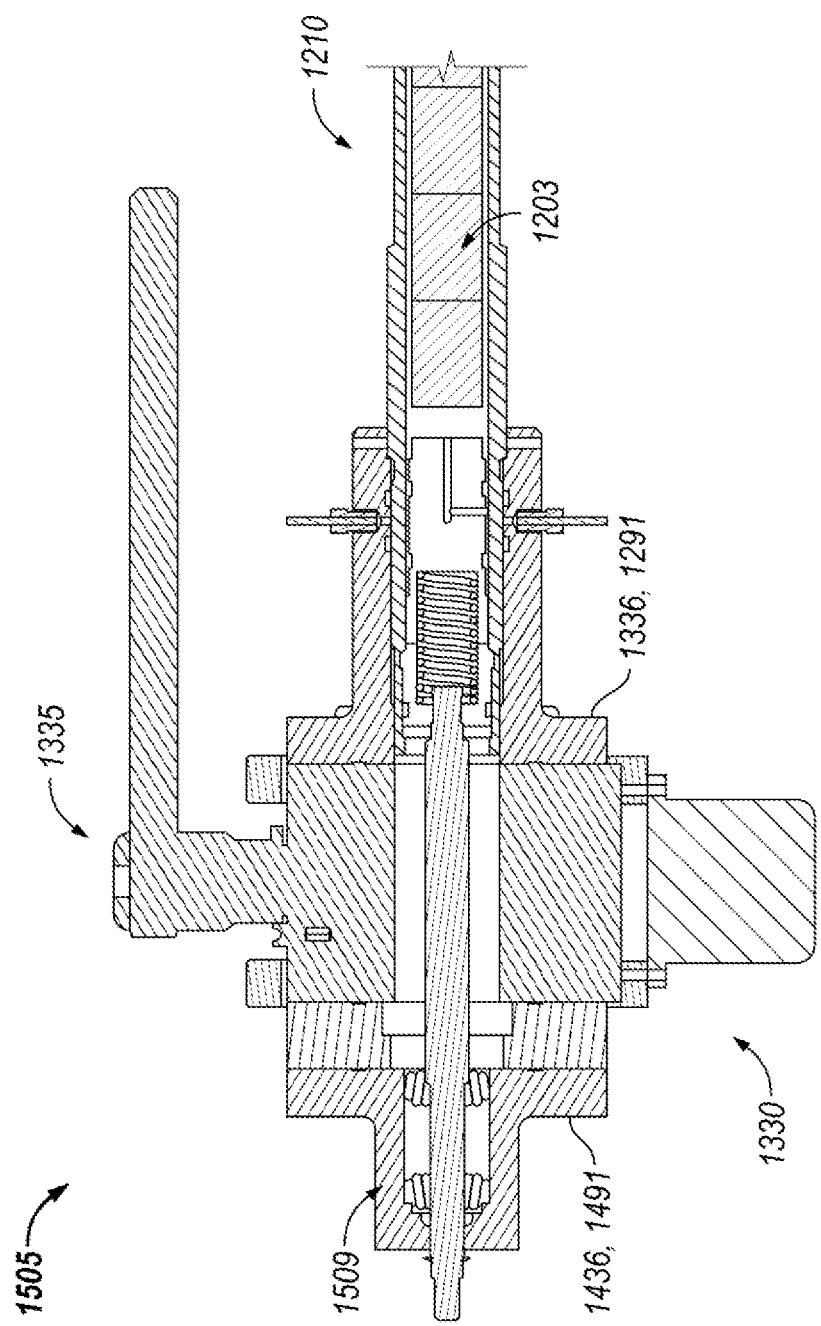

In step 1505, shown in FIG. 15 and some period of time after step 1305, the plug of the retrieval vessel 1210 is broken loose. For example, a plug breaker assembly 1509 is installed onto the valve 1335 and fastened with coupling features (e.g., bolts) of the valve 1335 properly. A user can then pressurize, using the hydraulic device, the valve 1335 and the internal volume of the plug breaker assembly 1509 with a fluid (e.g., fluorinert) to a pressure equal to the sampling pressure of the core samples within the retrieval vessel 1210. Doing so equalizes pressure across the plug of the retrieval vessel 1210 and eliminate any differential pressure, preload, and/or friction induced by differential pressure loads.

By rotating the plug breaker assembly 1509 with sufficient torque (e.g., 350 ft*lbf) until the plug of the retrieval vessel 1210 is broken loose. If needed, a user can apply an opposing rotation (e.g., clockwise torque of 30 ft*lbf) to re-seat/re-torque, to a lesser degree, the plug in the retrieval vessel 1210. A user can then isolate the pressure to the cavity of the retrieval vessel 1210 by moving the valve 1335 to the fully closed position. A user can also then bleed pressure and fluid from the internal volume of the plug breaker assembly 1509. The plug breaker assembly 1509 can then be removed from the valve 1335. Some of the core samples 1203 are shown within the retrieval vessel 1210 in FIG. 15.

Figure 16:
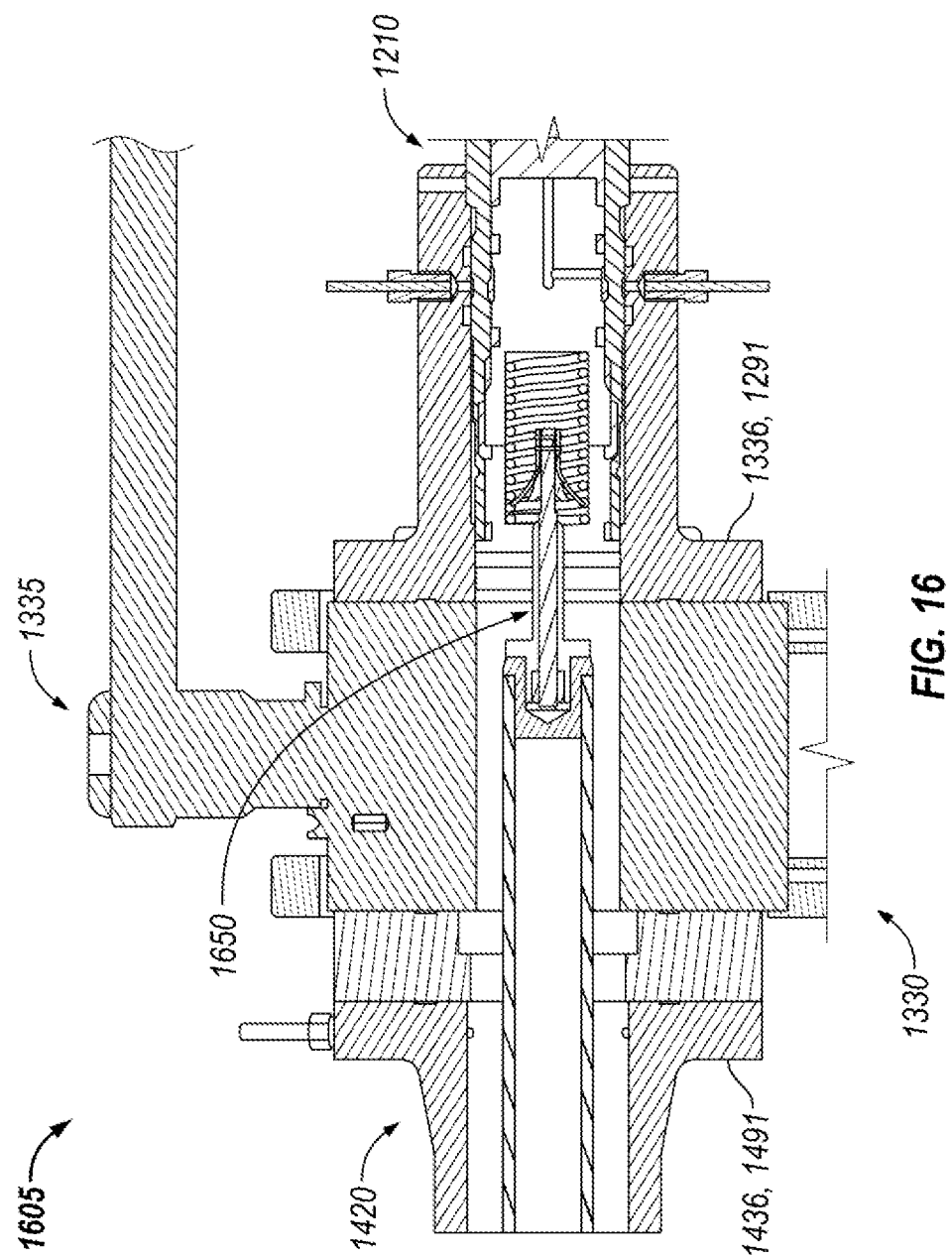

In step 1605, shown in FIG. 16 and some period of time after step 1505, the plug hex of the retrieval vessel 1210 is engaged. The linear actuator 1420 is installed in this step 1605. A user can remove the coupling features 1336 (e.g., bolts) from step 1305 above and slide the pressurized retrieval vessel 1210 away from the valve 1355 by some distance (e.g., about 6 inches). A user can also secure the CVFO brackets. An extractor 1650 (also sometimes called a plug removal head) can then be installed and secured to the rod of the linear actuator 1420.

If the linear actuator 1420 is not already coupled to the valve 1355 of the valve assembly 1350, then the coupling features 1491 of the linear actuator 1420 are coupled to the coupling features 1436 of the valve 1355 using bolts. Once the valve 1355 is fully open and the linear actuator 1420 is in the start (e.g., home, zero) position, a user can advance the linear actuator 1420 through the valve 1355 by a certain distance (e.g., 10 inches). A user can then verify that the extractor 1650 protrudes past the face of the valve 1355 by some distance (e.g., 2.77 inches). A user can then recouple the combined retrieval vessel 1210/adapter flange 1296 to the coupling features 1336 of the valve 1355 with the plug removal head engaged through the plug hex of the retrieval vessel 1210.

Once this is accomplished, the plug and spring of the retrieval vessel 1210 are removed. For example, a user can install a high-pressure hydraulic line to the lower port of the linear actuator 1420. The inner chamber of the retrieval vessel 1210 can then be isolated by closing the pressure port. A user can then vent the upper plug and pressurize the combined system with the hydraulic device until fluid trickles from the upper port, which removes all air from the combined volume. The upper port is then closed. The pressure of the combined system can then be adjusted to the internal pressure of the retrieval vessel 1210 by adjusting a pressure relief/over pressure valve and air driven pump of the hydraulic device.

Once this is done, the user can unthread the hex plug of the retrieval vessel 1210 to fully disengage the hex plug from the vessel. The linear actuator 1420 can then be returned to the home position, which draws out the plug and spring of the retrieval vessel 1210 by the extractor 1650. Afterwards, the valve 1355 can be moved to the fully closed position, and the pressure valve of the linear actuator 1420 can be closed. The bleed valve of the linear actuator 1420 can then be opened, and the resulting fluid can be purged to the excess fluid catch tank (e.g., excess fluid catch tank 1197). The user can then retract the linear actuator 1420 and remove the plug and spring from the linear actuator 1420.

Figure 17:
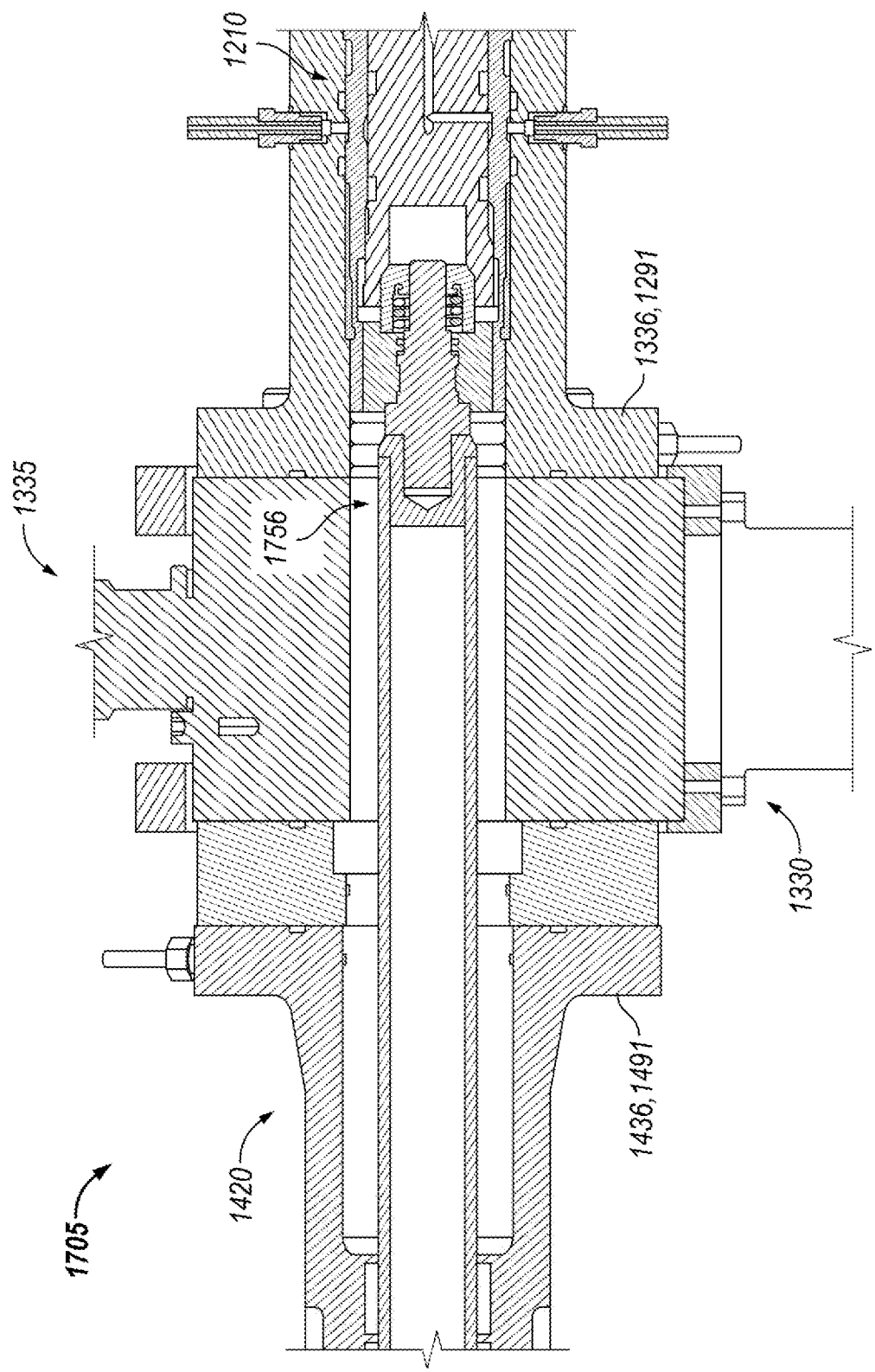

In step 1705, shown in FIG. 17 and some period of time after step 1605, the piston of the retrieval vessel 1210 is removed. For example, the piston head removal assembly 1756 can be inserted into the linear actuator 1420. If the linear actuator 1420 is not already coupled to the valve 1335 of the valve assembly 1330, then the coupling features 1436 of the valve 1335 should engage the linear actuator 1420. In either case, the valve 1335 is in the fully closed position. The working chamber of the linear actuator can then be pressurized using the hydraulic device until the pressure of the working chamber equals the sampling pressure of the retrieval vessel 1210. Once this is done, the valve 1335 is moved to the fully open position.

At this point, the linear actuator 1420 is operated to move the piston head removal assembly 1756 through the valve 1335 into the retrieval vessel 1210 by some distance (e.g., 11.5 inches) until the piston head removal assembly 1756 contacts the piston within the retrieval vessel 1210. By rotating the shaft of the linear actuator 1420 in a direction (e.g., counterclockwise), the threads of the piston align with the threads of the piston head removal assembly 1756, the piston head removal assembly 1756 becomes properly aligned to engage the piston. At that point, by rotating the shaft of the linear actuator 1420 in the opposite direction (e.g., clockwise), the piston head removal assembly 1756 engages the piston. By continuing to rotate the shaft of the linear actuator 1420 in the same direction (e.g., translating to one-half of an inch, six full turns), the piston head removal assembly 1756 becomes fully engaged with the piston.

The shaft of the linear actuator can then be retracted, pulling the piston head removal assembly 1756 and the piston together through the valve 1335 into the linear actuator. The valve 1335 can then be moved to the fully closed position to isolate and maintain the sampling pressure within the retrieval vessel 1210. To assist in maintaining this sampling pressure, the hydraulic device can be used to ensure that the sampling pressure level is maintained in the retrieval vessel 1210. Any fluid in the linear actuator 1420 can be drained, and the joint piston head removal assembly 1756 and piston can be removed from the linear actuator 1420.

Figure 18:
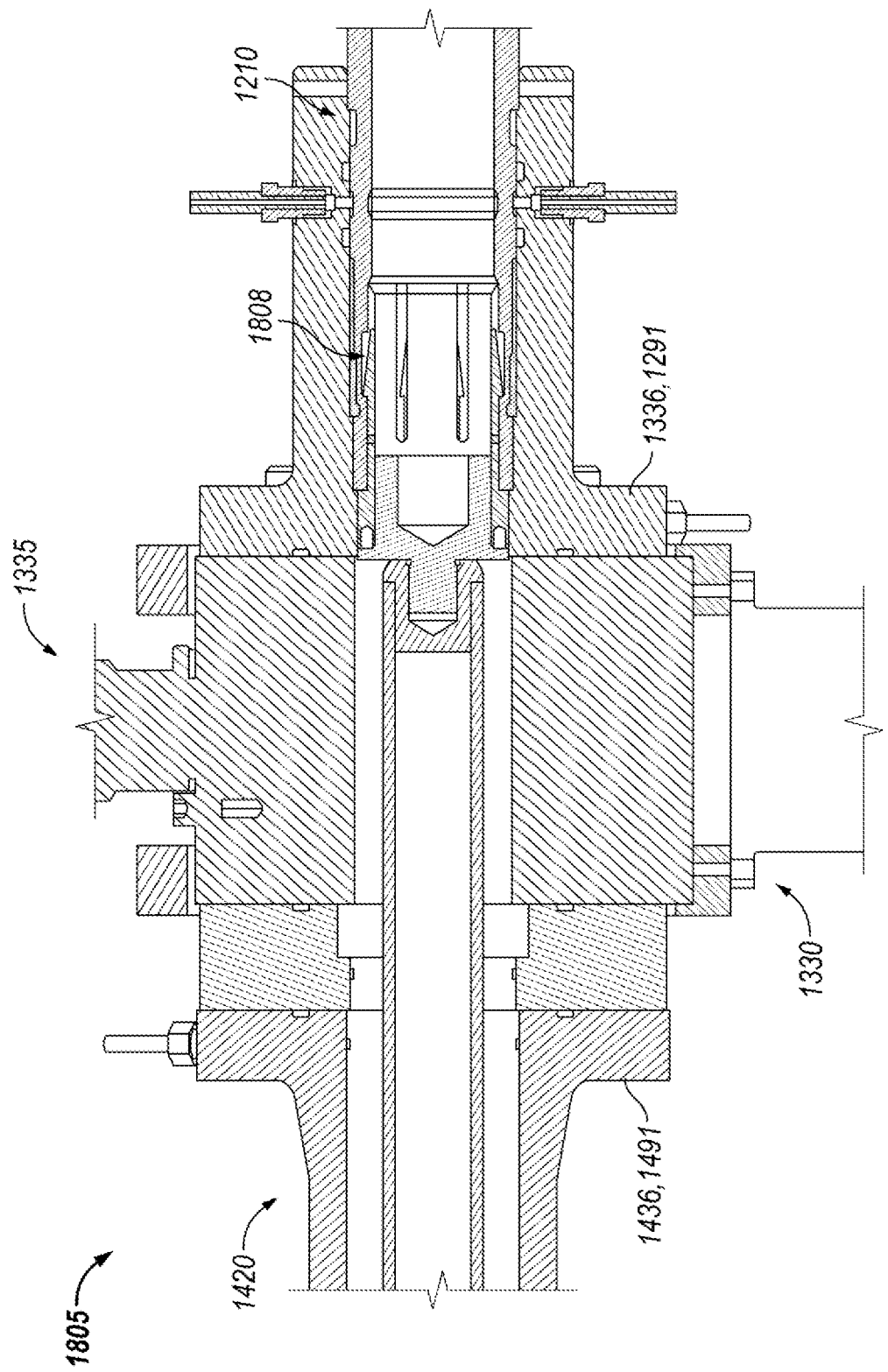

In step 1805, shown in FIG. 18 and some period of time after step 1705, a sleeve 1808 is installed. For example, with the valve 1335 in the fully closed position, the sleeve 1808 can be placed in the linear actuator 1420. If the linear actuator 1420 is not already coupled to the valve 1335 of the valve assembly 1330, then the coupling features 1436 of the valve 1335 should couple to the coupling features 1491 of the linear actuator 1420. The working chamber of the linear actuator 1420 can then be pressurized using the hydraulic device until the pressure of the working chamber equals the sampling pressure of the retrieval vessel 1210. Once this is done, the valve 1335 is moved to the fully open position.

At this point, the linear actuator 1420 is operated to move the sleeve 1808 through the valve 1335 into the retrieval vessel 1210 by some distance (e.g., 10.85 inches) until the sleeve 1808 is installed in the retrieval vessel 1210. The shaft of the linear actuator can then be retracted, leaving the sleeve in the retrieval vessel 1210. The valve 1335 can then be moved to the fully closed position to isolate and maintain the sampling pressure within the retrieval vessel 1210. To assist in maintaining this sampling pressure, the hydraulic device can be used to ensure that the sampling pressure level is maintained in the retrieval vessel 1210. Any fluid in the linear actuator 1420 can be drained. The linear actuator 1420 can then be decoupled from the valve 1335.

After this, while not shown in a figure, the subterranean core samples are transferred from the retrieval vessel 1210 to the testing vessel assembly (e.g., testing vessel assembly 740). For example, with the valve 1335 in the fully closed position, the testing vessel assembly can be directly coupled to the valve 1335 of the valve assembly 1330 using the coupling features 1436 of the valve 1335. The testing vessel assembly can then be pressurized using the hydraulic device until the pressure of the testing vessel assembly equals the sampling pressure of the retrieval vessel 1210. Once this is done, the valve 1335 is moved to the fully open position.

Then, the assembly of the valve 1335, the testing vessel assembly, and the retrieval vessel 1210 is rotated vertically so that the retrieval vessel 1210 is located higher than the valve 1335. At this point, a vibrating device (e.g., vibrating device 281) and/or a heating device (e.g., heating device 282) applied to the retrieval vessel 1210 can be operated. While maintaining this vertical orientation, gravity will cause the subterranean core samples to drop into the testing vessel assembly. This transfer process can take some amount of time (e.g., 5 minutes, 30 minutes). When the transfer process is complete, the valve 1335 is moved to the fully closed position, and the assembly of the valve 1335, the testing vessel assembly, and the retrieval vessel 1210 is rotated back to a horizontal position. With the chamber of the retrieval vessel 1210 now void of the subterranean core samples, the retrieval vessel 1210 can be depressurized and drained, and the retrieval vessel 1210 can be decoupled from the valve 1335.

Figure 19:
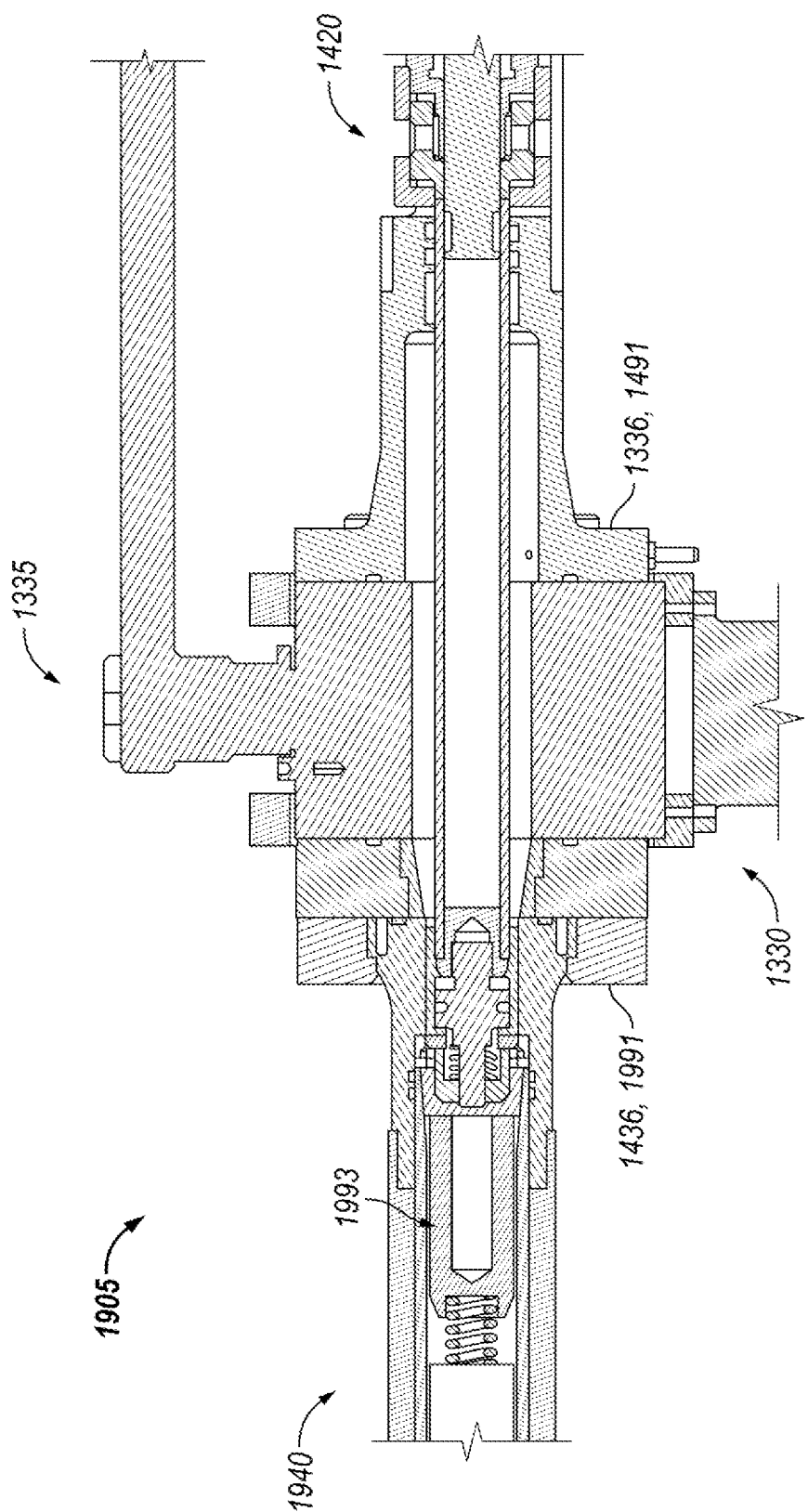
Figure 20:
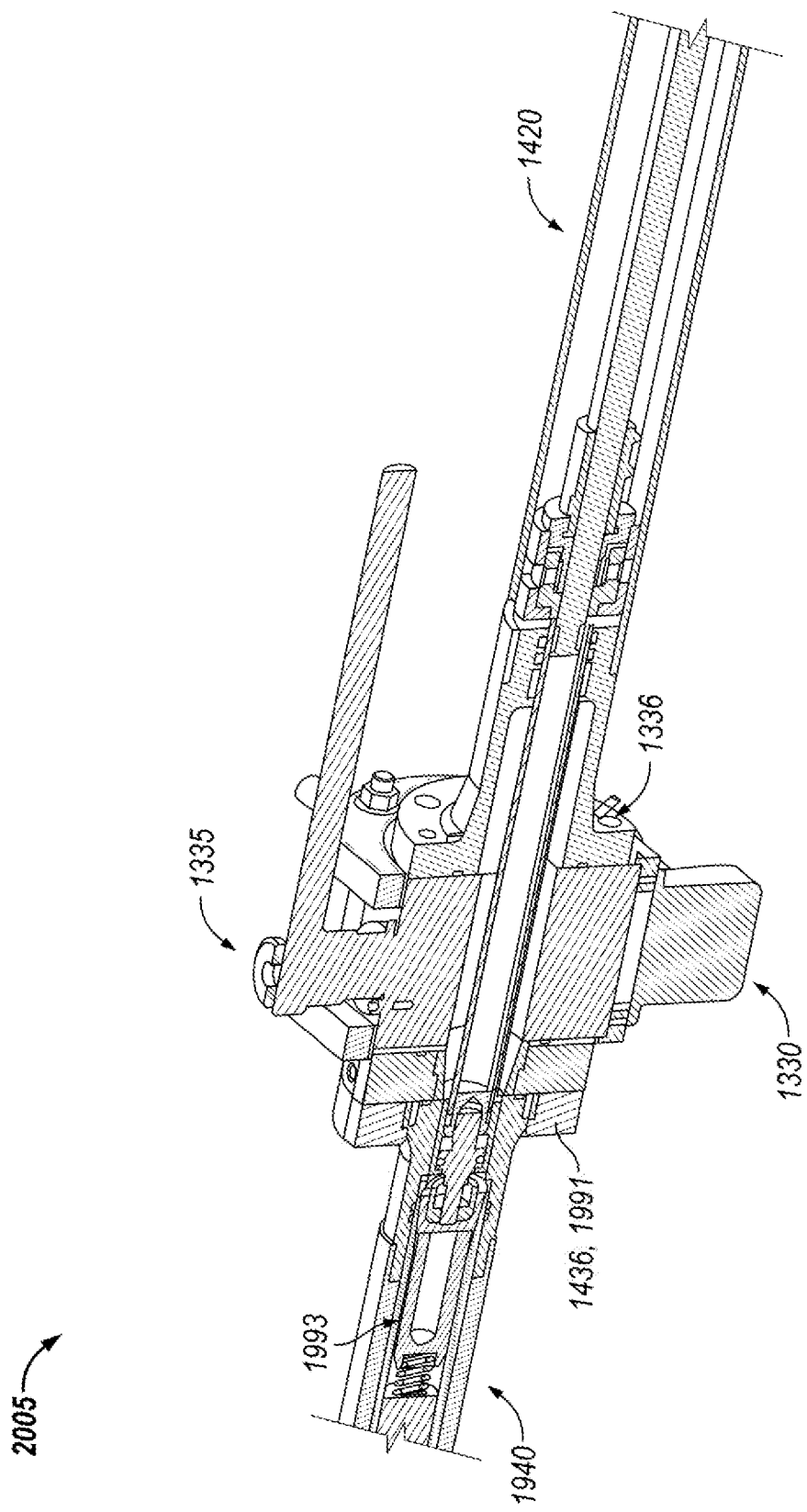

In step 1905, shown in FIGS. 19 and 20 and some period of time after step 1805, a core spacer assembly 1993 is inserted. With the coupling features 1991 of the testing vessel assembly 1940 still indirectly (using bolts) coupled to the coupling features 1336 of the valve 1335, and with the valve 1335 in the fully closed position, the core spacer assembly 1993 with piston head removal is inserted into the linear actuator 1420, and the linear actuator 1420 is coupled to the valve 1335 of the valve assembly 1330 using the coupling features 1336 of the valve 1335 and the coupling features 1491 of the linear actuator 1420. The working chamber of the linear actuator 1420 can then be pressurized using the hydraulic device until the pressure of the working chamber equals the sampling pressure of the testing vessel assembly 1940. Once this is done, the valve 1335 is moved to the fully open position.

At this point, the linear actuator 1420 can be advanced by some distance (e.g., 12 inches), pushing the core spacer assembly 1993 forward. The linear actuator 1420 can then be retracted. When the linear actuator 1420 is retracted, the core spacer assembly 1993 remains within the testing vessel 1940. The valve 1335 can then be moved to the fully closed position to isolate and maintain the sampling pressure within the testing vessel 1940. To assist in maintaining this sampling pressure, the hydraulic device can be used to ensure that the sampling pressure level is maintained in the testing vessel 1940. Any fluid in the linear actuator 1420 can be drained. The linear actuator 1420 can then be decoupled from the valve 1335.

Figure 21:
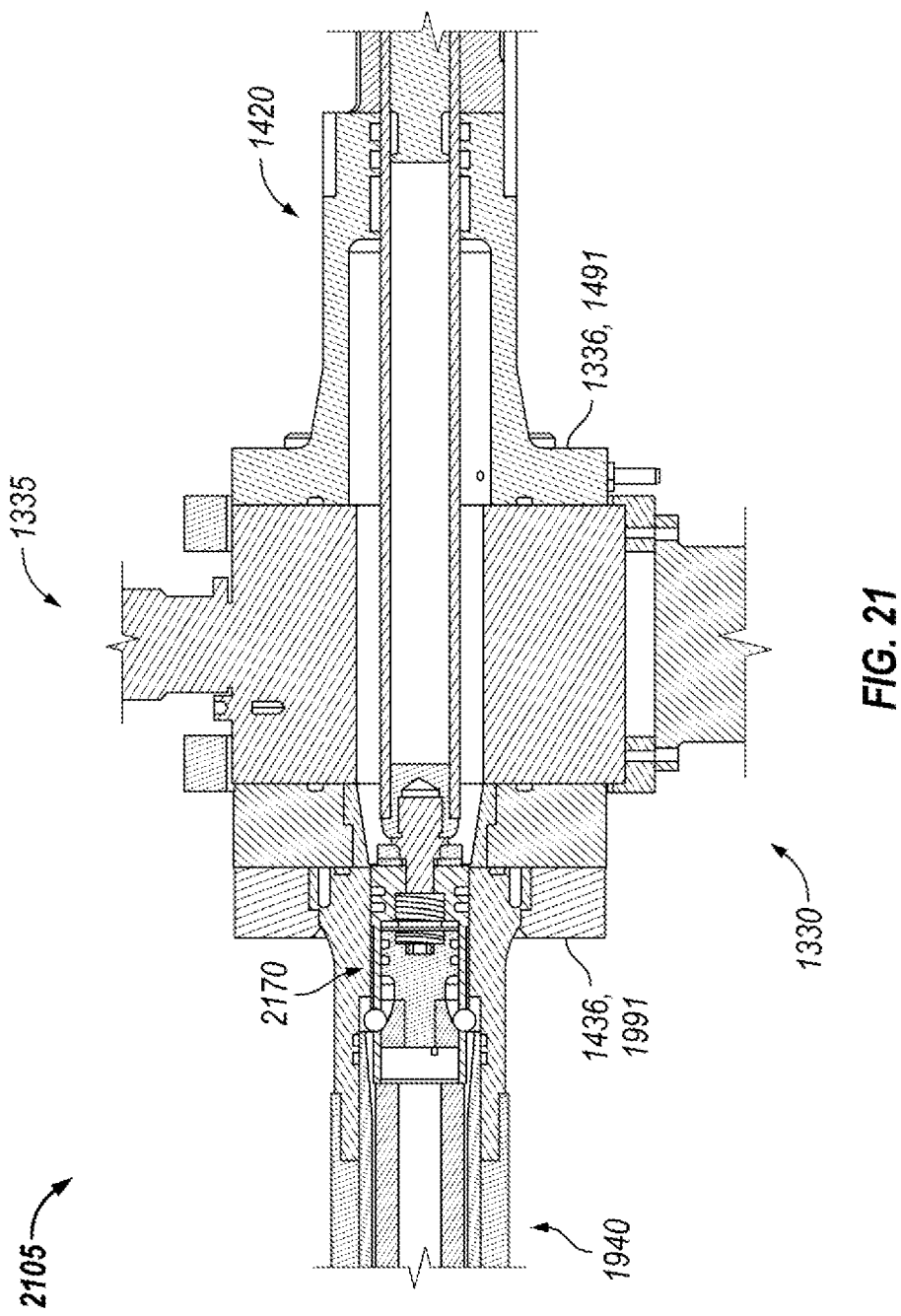

In step 2105, shown in FIG. 21 and some period of time after step 1905, a testing vessel plug assembly 2170 is installed. For example, with the valve 1335 in the fully closed position, the testing vessel plug assembly 2170 can be placed in the linear actuator 1420. If the linear actuator 1420 is not already coupled to the valve 1335 of the valve assembly 1330, then the coupling features 1336 of the valve 1335 should couple to the coupling features 1491 of the linear actuator 1420. The working chamber of the linear actuator 1420 can then be pressurized using the hydraulic device until the pressure of the working chamber equals the sampling pressure of the testing vessel 1210. Once this is done, the valve 1335 is moved to the fully open position.

At this point, the linear actuator 1420 can be advanced by some distance (e.g., 10.57 inches), pushing the testing vessel plug assembly 2170 forward and into position relative to the testing vessel 1940. When the testing vessel plug assembly 2170 is pushed far enough forward, the testing vessel plug assembly 2170 becomes installed relative to the testing vessel 1940. Once installed, the testing vessel plug assembly 2170 keeps the testing vessel 1940 pressurized at the sampling pressure. The linear actuator 1420 can then be retracted. When the linear actuator 1420 is retracted, the testing vessel plug assembly 2170 remains coupled to the testing vessel 1940. The valve 1335 can then be moved to the fully closed position to isolate and maintain the sampling pressure within the testing vessel 1940. To assist in maintaining this sampling pressure, the hydraulic device can be used to ensure that the sampling pressure level is maintained in the testing vessel 1940. Any fluid in the linear actuator 1420 can be drained. The linear actuator 1420 can then be decoupled from the valve 1335.

Finally, the testing vessel 1940 can be decoupled from the valve 1335, at which time the subterranean core samples within testing vessel 1940 and maintained at sampling pressure can be tested through the testing vessel 1940 because the testing vessel 1940 is made of non-magnetic material, non-metallic material, and/or some other material that has a low noise profile when exposed to testing such as using NMR.

FIGS. 22A through 22E show a system 2299 at a time when pressurized reservoir core samples 2203 are transferred in accordance with certain example embodiments. Referring to FIGS. 1 through 22E, the sequence shown in FIGS. 22A through 22E corresponds to some of what is described in step 1905 of FIG. 19 above. The system 2299 of FIGS. 22A through 22E includes a frame 2295 on which is mounted a valve assembly 2230, to which is coupled a retrieval vessel 2210 and a testing vessel 2240. The valve assembly 2230 also includes a vibrating device 2281. These components of the system 2299 are substantially the same as the corresponding components discussed above with respect to FIGS. 1 through 21.

Figure 22A:
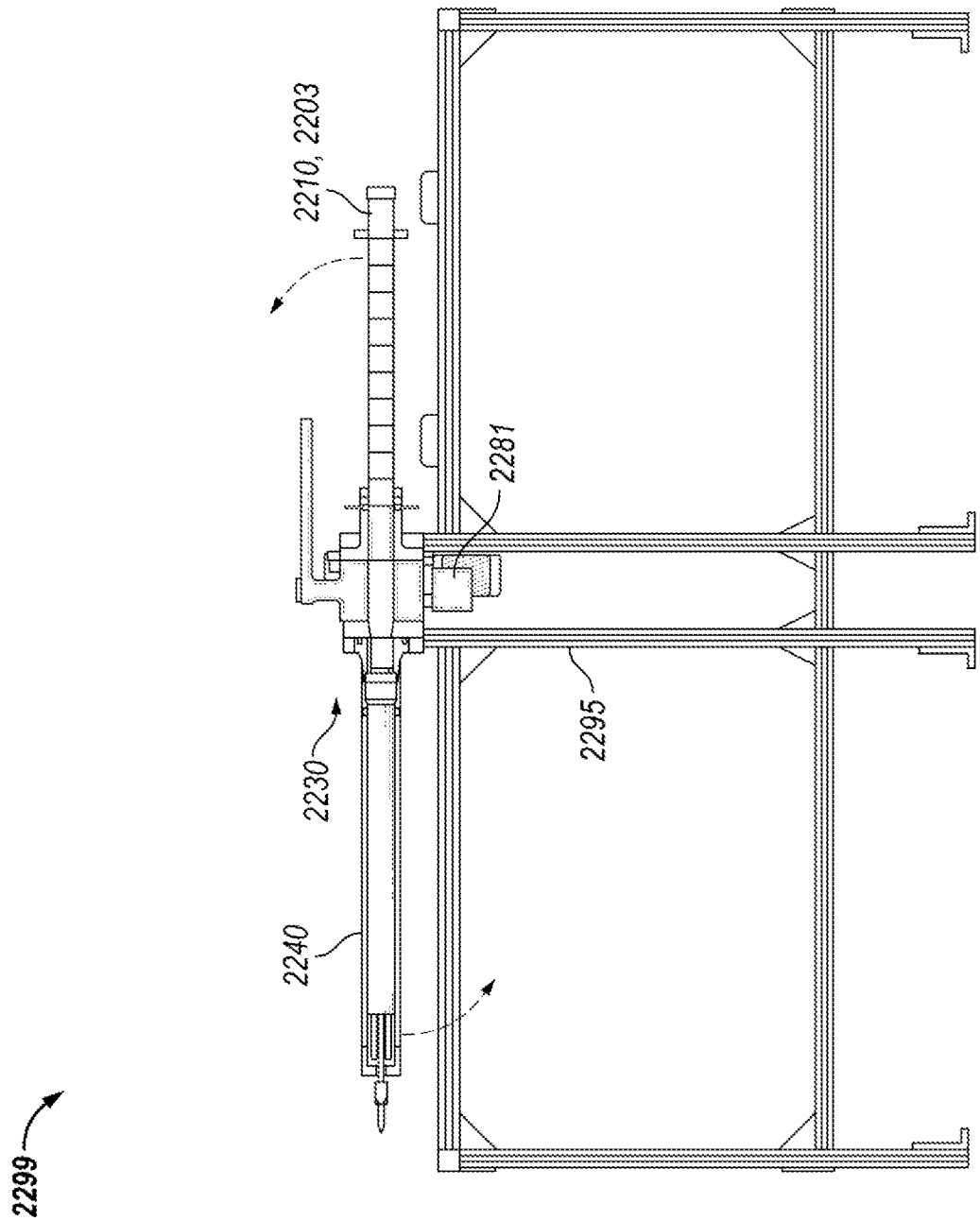
FIGS. 22A through 22E show a system at a time when pressurized reservoir core samples are transferred in accordance with certain example embodiments.
Figure 22B:
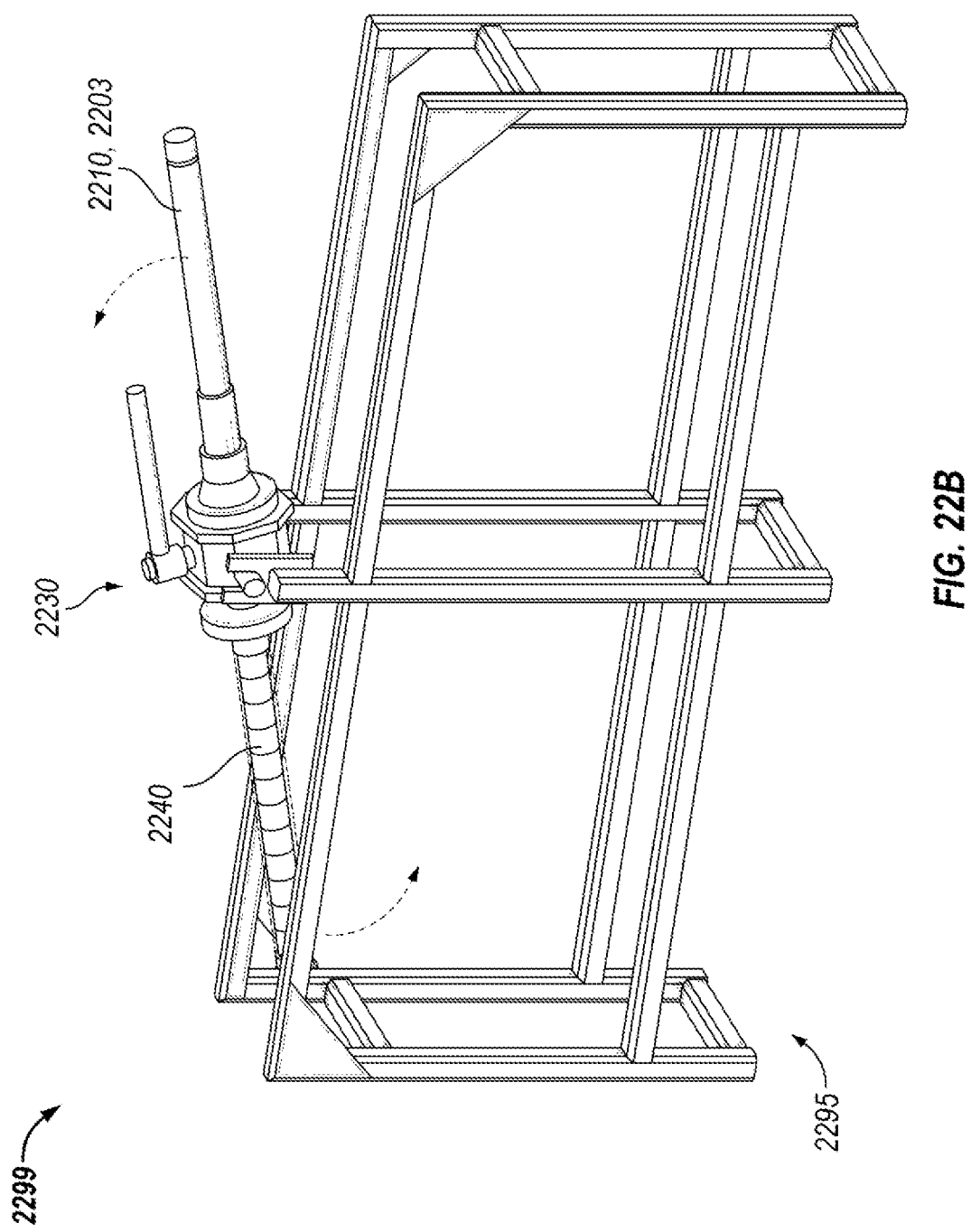

In FIG. 22A, the valve of the valve assembly 2230, the retrieval vessel 2210, and the testing vessel 2240 are oriented such that the retrieval vessel 2210 and the testing vessel 2240 are horizontal relative to the ground on which the frame 2295 sits. The subterranean core samples 2203 are disposed inside the retrieval vessel 2210. The pressure within the assembly of the valve assembly 2230, the retrieval vessel 2210, and the testing vessel 2240 is substantially the sampling pressure at which the subterranean core samples 2203 were taken. In FIG. 22B, the assembly of the valve assembly 2230, the retrieval vessel 2210, and the testing vessel 2240 begin rotating about a gimbal between the valve assembly 2230 and the frame 2295. The rotation in FIG. 22B puts the retrieval vessel 2210 slightly above the valve assembly 2230 and the testing vessel 2240 slightly below the valve assembly 2230.

Figure 22C:
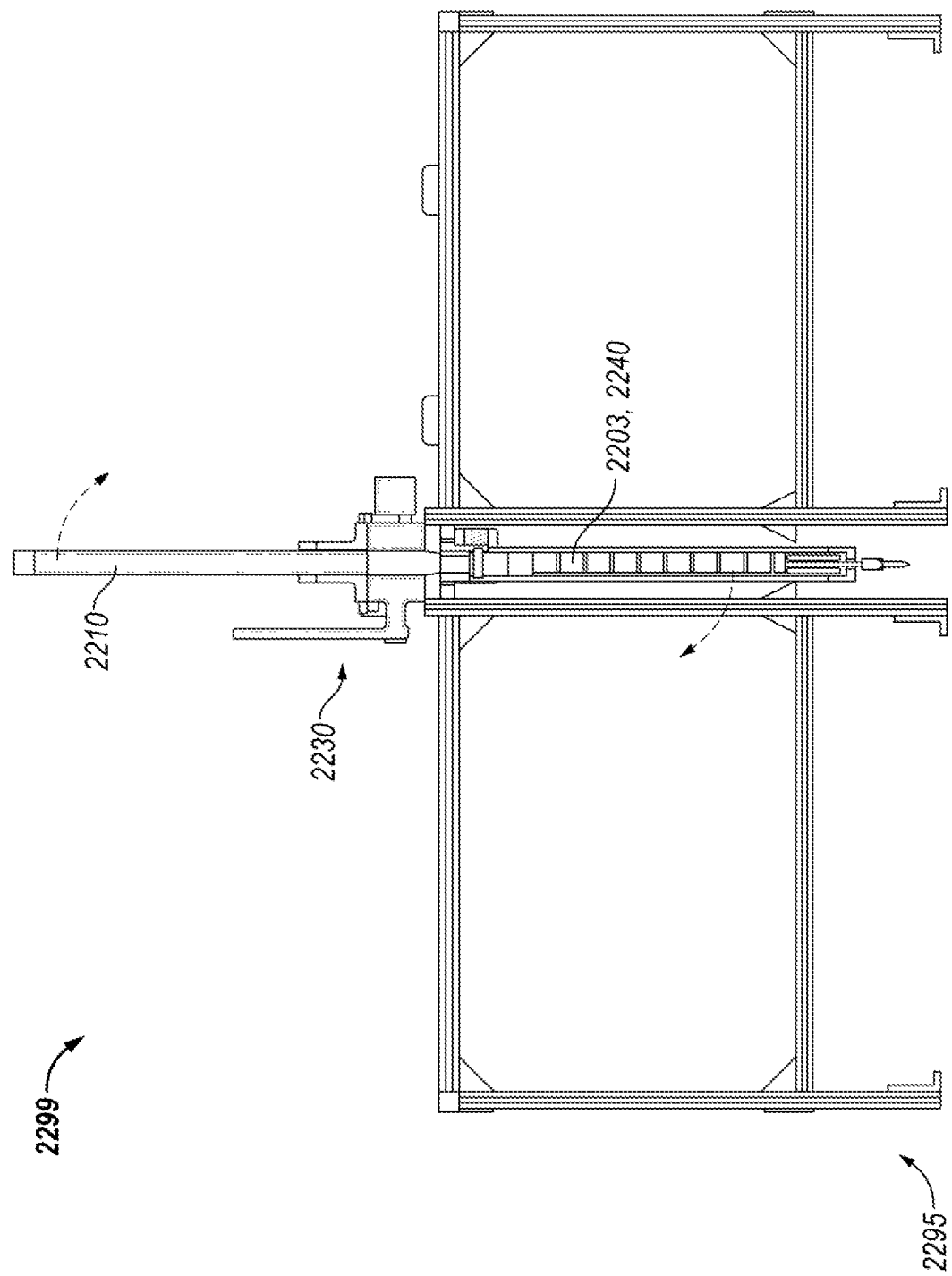
Figure 22D:
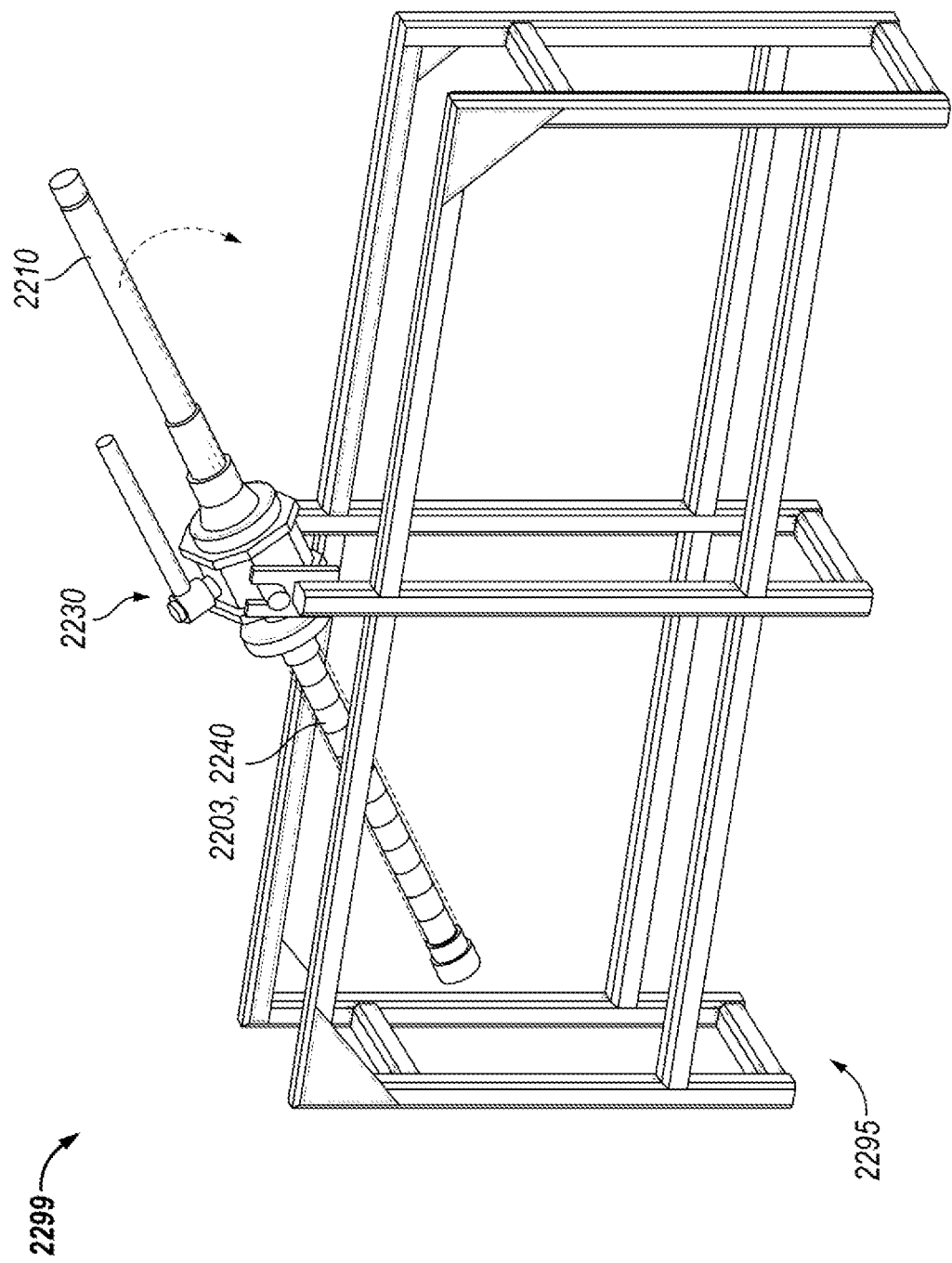
Figure 22E:
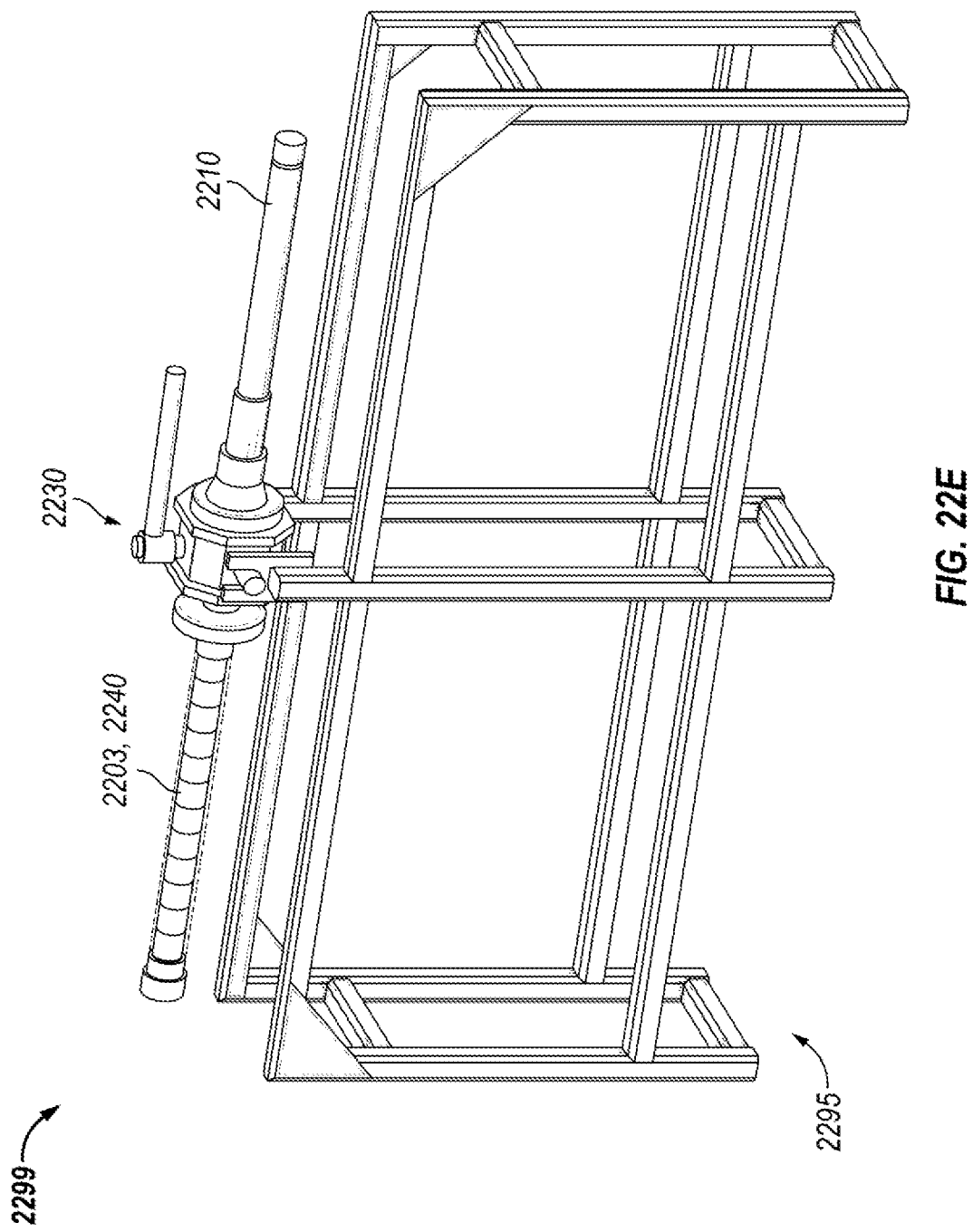

In FIG. 22C, the assembly of the valve assembly 2230, the retrieval vessel 2210, and the testing vessel 2240 continues its rotation until the assembly is vertical. The subterranean core samples 2203, assisted by gravity, the vibrating device 2281, and/or an optional heating device (e.g., heating device 282) slide through the valve of the valve assembly 2230 and into the testing vessel 2240. In FIG. 22D, the assembly of the valve assembly 2230, the retrieval vessel 2210, and the testing vessel 2240 retraces its path toward horizontal, with the subterranean core samples 2203 remaining in the testing vessel 2240 under the sampling pressure. In FIG. 23E, the assembly of the valve assembly 2230, the retrieval vessel 2210, and the testing vessel 2240 returns to a horizontal orientation, and the subterranean core samples 2203 remaining in the testing vessel 2240 under the sampling pressure.

Figure 23:
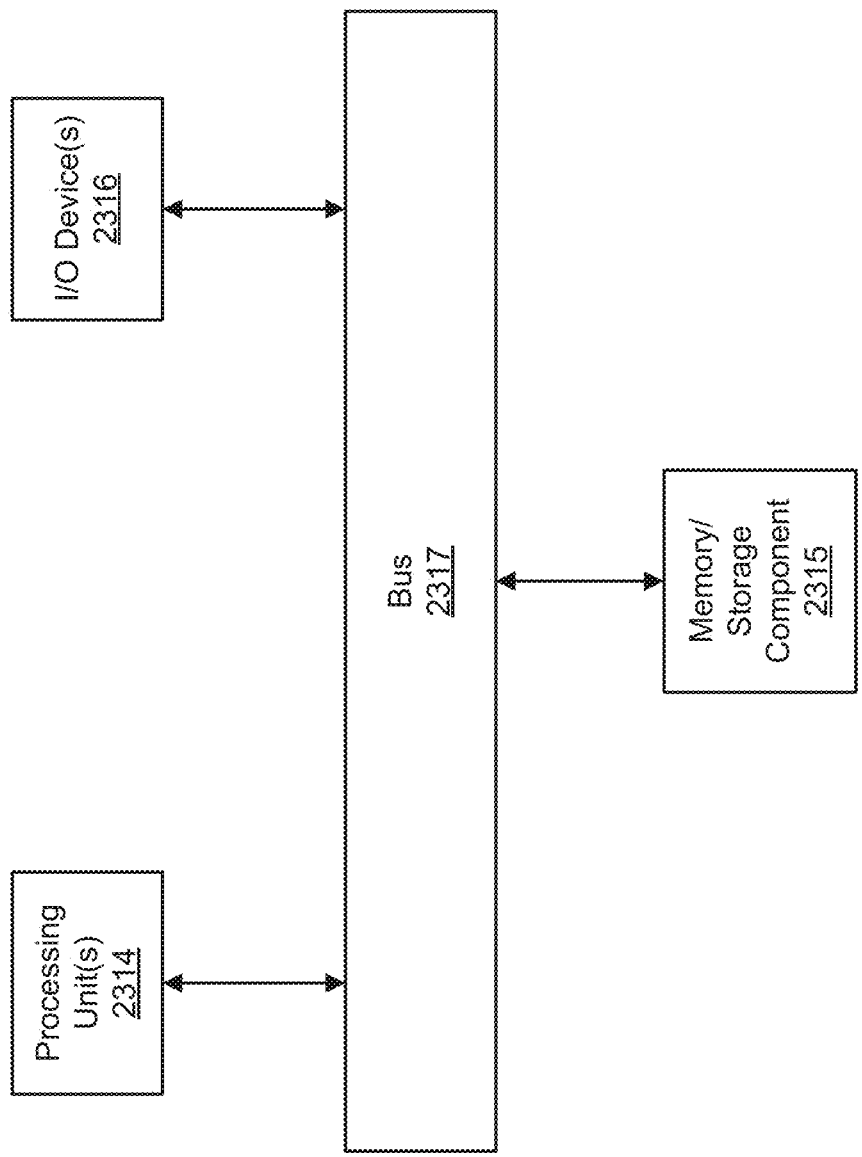
FIG. 23 shows a computing device in accordance with certain example embodiments.

FIG. 23 shows a computing device in accordance with certain example embodiments. FIG. 23 illustrates one embodiment of a computing device 2318 that implements one or more of the various techniques described herein, and which is representative, in whole or in part, of the elements described herein pursuant to certain exemplary embodiments. For example, the controller 204 of FIG. 2 and its various components (e.g., hardware processor, memory, control engine) can be considered a computing device 2318 as in FIG. 2. Computing device 2318 is one example of a computing device and is not intended to suggest any limitation as to scope of use or functionality of the computing device and/or its possible architectures. Neither should computing device 2318 be interpreted as having any dependency or requirement relating to any one or combination of components illustrated in the example computing device 2318.

Computing device 2318 includes one or more processors or processing units 2314, one or more memory/storage components 2315, one or more input/output (I/O) devices 2316, and a bus 2317 that allows the various components and devices to communicate with one another. Bus 2317 represents one or more of any of several types of bus structures, including a memory bus or memory controller, a peripheral bus, an accelerated graphics port, and a processor or local bus using any of a variety of bus architectures. Bus 2317 includes wired and/or wireless buses.

Memory/storage component 2315 represents one or more computer storage media. Memory/storage component 2315 includes volatile media (such as random access memory (RAM)) and/or nonvolatile media (such as read only memory (ROM), flash memory, optical disks, magnetic disks, and so forth). Memory/storage component 2315 includes fixed media (e.g., RAM, ROM, a fixed hard drive, etc.) as well as removable media (e.g., a Flash memory drive, a removable hard drive, an optical disk, and so forth).

One or more I/O devices 2316 allow a customer, utility, or other user to enter commands and information to computing device 2318, and also allow information to be presented to the customer, utility, or other user and/or other components or devices. Examples of input devices include, but are not limited to, a keyboard, a cursor control device (e.g., a mouse), a microphone, a touchscreen, and a scanner. Examples of output devices include, but are not limited to, a display device (e.g., a monitor or projector), speakers, outputs to a lighting network (e.g., DMX card), a printer, and a network card.

Various techniques are described herein in the general context of software or program modules. Generally, software includes routines, programs, objects, components, data structures, and so forth that perform particular tasks or implement particular abstract data types. An implementation of these modules and techniques are stored on or transmitted across some form of computer readable media. Computer readable media is any available non-transitory medium or non-transitory media that is accessible by a computing device. By way of example, and not limitation, computer readable media includes "computer storage media".

"Computer storage media" and "computer readable medium" include volatile and non-volatile, removable and non-removable media implemented in any method or technology for storage of information such as computer readable instructions, data structures, program modules, or other data. Computer storage media include, but are not limited to, computer recordable media such as RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which is used to store the desired information and which is accessible by a computer.

The computer device 2318 is connected to a network (not shown) (e.g., a LAN, a WAN such as the Internet, cloud, or any other similar type of network) via a network interface connection (not shown) according to some exemplary embodiments. Those skilled in the art will appreciate that many different types of computer systems exist (e.g., desktop computer, a laptop computer, a personal media device, a mobile device, such as a cell phone or personal digital assistant, or any other computing system capable of executing computer readable instructions), and the aforementioned input and output means take other forms, now known or later developed, in other exemplary embodiments. Generally speaking, the computer system 2318 includes at least the minimal processing, input, and/or output means necessary to practice one or more embodiments.

Further, those skilled in the art will appreciate that one or more elements of the aforementioned computer device 2318 is located at a remote location and connected to the other elements over a network in certain exemplary embodiments. Further, one or more embodiments is implemented on a distributed system having one or more nodes, where each portion (e.g., control engine) of the implementation is located on a different node within the distributed system. In one or more embodiments, the node corresponds to a computer system. Alternatively, the node corresponds to a processor with associated physical memory in some exemplary embodiments. The node alternatively corresponds to a processor with shared memory and/or resources in some exemplary embodiments.

The systems, methods, and apparatuses described herein allow for transferring pressurized reservoir core samples. Example embodiments can maintain core samples at the same or other managed pressure and transfer these core samples at that same pressure into a testable vessel so that the core samples can be tested as if they were in situ within the subterranean formation in terms of pressure. As a result, example embodiments allow for more reliable and controlled testing and test results of core samples compared to embodiments currently used in the art.

Although embodiments described herein are made with reference to example embodiments, it should be appreciated by those skilled in the art that various modifications are well within the scope and spirit of this disclosure. Those skilled in the art will appreciate that the example embodiments described herein are not limited to any specifically discussed application and that the embodiments described herein are illustrative and not restrictive. From the description of the example embodiments, equivalents of the elements shown therein will suggest themselves to those skilled in the art, and ways of constructing other embodiments using the present disclosure will suggest themselves to practitioners of the art. Therefore, the scope of the example embodiments is not limited herein.

What is claimed is:

1. A system for transferring at least one subterranean core sample under pressure, the system comprising:
    a retrieval vessel that collects and houses the at least one subterranean core sample at a sampling pressure at which the at least one subterranean core sample is collected;
    a valve having an open position and a closed position;
    a linear actuator that couples to the retrieval vessel through the valve when the valve is in the open position at a first time, wherein the linear actuator facilitates removal of at least one pressure barrier from the retrieval vessel through the valve at the first time while maintaining the sampling pressure of the at least one subterranean sample;
    a testing vessel that couples to the linear actuator through the valve when the valve is in the open position at a second time; and
    a hydraulic device that facilitates pressurizing the testing vessel to the sampling pressure at the second time,
    wherein the testing vessel and the retrieval vessel are coupled to each other through the valve at a third time, wherein the at least one subterranean core sample is transferred from the retrieval vessel through the valve to the testing vessel at the third time at the sampling pressure when the valve is in the open position,
    wherein the linear actuator installs a pressure barrier in the testing vessel, and
    wherein the at least one subterranean core sample, once transferred to the testing vessel, is tested at a fourth time while in the testing vessel at the sampling pressure.

2. The system of claim 1, wherein the testing vessel comprises measurement zone, wherein the measurement zone comprises at least one of a group consisting of a non-metallic material and a non-magnetic material.

3. The system of claim 1, wherein the testing vessel, the retrieval vessel, and the valve are oriented at the third time so that the retrieval vessel is disposed above the testing vessel to allow gravity to move the at least one subterranean core sample from the retrieval vessel to the testing vessel.

4. The system of claim 1, further comprising:
    a heating device that applies heat to the retrieval vessel during the third time.

5. The system of claim 1, further comprising:
    a vibrating device that vibrates the retrieval vessel during the third time.

6. The system of claim 1, further comprising:
    an adapter flange that is coupled to the retrieval vessel before the first time.

7. The system of claim 1, further comprising:
    a piston removal tool of the linear actuator that removes a piston of the retrieval vessel during the first time.

8. The system of claim 1, further comprising:
    a hydraulic device that controls a pressure within the retrieval vessel, the linear actuator, and the testing vessel during the first time, the second time, and the third time.

9. The system of claim 1, further comprising:
    a core spacer assembly that is disposed between the retrieval vessel and the testing vessel after transferring the at least one subterranean core sample from the retrieval vessel to the testing vessel.

10. The system of claim 1, further comprising:
    a testing vessel plug that is used to seal the at least one subterranean core sample within the testing vessel at the sample pressure after the third time.

11. The system of claim 1, wherein the valve is a ball valve.

12. The system of claim 1, further comprising:
    an extractor tool that removes a plug of the retrieval vessel during the first time.

13. The system of claim 12, wherein the extractor tool further removes a spring of the retrieval vessel during the first time.

* * * * *